(12) United States Patent
Davis et al.

(10) Patent No.: US 7,202,349 B2
(45) Date of Patent: Apr. 10, 2007

(54) INTRINSICALLY FLUORESCENT, SELF-MULTIMERIZING MHC FUSION PROTEINS AND COMPLEXES THEREOF

(75) Inventors: Kenneth A. Davis, Mountain View, CA (US); Bing-Yuan Wei, San Diego, CA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 481 days.

(21) Appl. No.: 10/045,949

(22) Filed: Jan. 11, 2002

(65) Prior Publication Data

US 2002/0115157 A1 Aug. 22, 2002

Related U.S. Application Data

(60) Provisional application No. 60/261,448, filed on Jan. 12, 2001.

(51) Int. Cl.
*C07K 14/74* (2006.01)
*G01N 33/53* (2006.01)
*G01N 33/532* (2006.01)
*C12N 5/10* (2006.01)

(52) U.S. Cl. ............... 530/402; 530/403; 435/7.1; 435/7.2; 435/325; 435/975

(58) Field of Classification Search ........... 530/388.75, 530/389.6, 391.3, 402, 403; 435/7.1, 7.21, 435/325, 975
See application file for complete search history.

(56) References Cited

U.S. PATENT DOCUMENTS

| 4,902,613 A * | 2/1990 | Chang et al. ............ 435/2 |
| 5,635,363 A | 6/1997 | Altman et al. |
| 5,804,387 A | 9/1998 | Cormack et al. |
| 6,015,884 A | 1/2000 | Schneck et al. |
| 6,090,919 A | 7/2000 | Cormack et al. |
| 6,140,113 A | 10/2000 | Schneck et al. |
| 6,232,445 B1 * | 5/2001 | Rhode et al. ............ 530/387.3 |

OTHER PUBLICATIONS

Doherty, P.C. et al, "Accessing Complexity: The Dynamics of Virus-Specific T Cell Responses," *Annual Review Immunology*, 18:561-592 (2000).
Ogg, G.S. et al, "Quantitation of Antigen-Specific CD8+ T-cell responses", *Immunology Letters*, 66(1-3):77-90 (1999).
Maini, M.K., et al, "T-cell Clonality in Immune Responses", *Immunology Today*, 20(6); 262-266 (1999).
Doherty, P.C., "The New Numerology of Immunity Mediated by Virus-Specific CD8+ T Cells", *Current Opinions in Microbiology*; 1(4):419-422 (1998).
Reichstetter, S. et al, "Distinct T Cell Interactions with HLA Class II Tetramers Characterize a Spectrum of TCR Affinities in the Human Antigen-Specific T-Cell Response[1]", *Journal of Immunology*, 165(12):6994-6998 (2000).
Kwok, W.W. et al, "HLA-DQ Tetramers Identify Epitope-Specific T Cells in Peripheral Blood of Herpes Simplex Virus Type 2-Infected Individuals: Direct Detection of Immunodominant Antigen-Responsive Cells[1]", *Journal of Immunology* 164(8):4244-4249 (2000).
Liu, C.P., et al, "Detection of Glutamic Acid Decarboxylase-Activated T Cells with 1-A$^{g7}$ Tetramers", *Proceedings of the National Academy of Sciences USA*, 97(26):14596-14601 (2000).
Novak, E.J., et al, "MHC Class II Tetramers Identify Peptide-Specific Human CD4+ T Cells Proliferating In Response to Influenza A Antigen", *Journal of Clinical Investigation*, 104(12):R63-7 (1999).
Crawford, F., et al, "Detection of Antigen-Specific T Cells with Multivalent Soluble Class II MHC Covalent Peptide Complexes", *Immunity*, 8:675-682 (1998).
Kozono, H., et al, "Production of Soluble MHC Class II Proteins with Covalently Bound Single Peptides", *Nature* 369;151-154 (1994).
Altman, J.D., et al, "Phenotypic Analysis of Antigen-Specific T Lymphocytes", *Science*, 274:94 (1996).
Matsui, K., et al, "Low Affinity Interaction of Peptide-MHC Complexes with T Cell Receptors", *Science*, 254:1788-1791 (1991).
Matsui, K., et al, "Kinetics of T-Cell Receptor Binding to Peptide/I-E$^k$ Complexes: Correlation of the Dissociation Rate with T-Cell Responsiveness", *Proceedings of the National Academy of Science USA*, 91:12862-12866 (1994).
Dal Porto, J., et al, "A Soluble Divalent Class I Major Histocompatibility Complex Molecule Inhibits Alloreactive T cells at Nanomolar Concentrations", *Proceedings of the National Academy of Science USA*, 90:6671-6675 (1993).
Greten, T.F., et al, "Direct Visualization of Antigen-Specific T Cells: HTLV-1 Tax11-19-Specific CD8+ T Cells are Activated in Peripheral Blood and Accumulate in Cerebrospinal Fluid from HAM/TSP Patients", *Proceedings of the National Academy of Science USA*, 95:7568-7573 (1998).
Hamad, A.R.A., et al, "Potent T Cell Activation with Dimeric Peptide-Major Histocompatibility Complex Class II Ligand: The Role of CD4 Coreceptor" *Journal of Experimental Medicine*, 188:1633-1640 (1998).
Galbraith, D.W., et al, "Flow Cytometric Analysis and FACS Sorting of Cells Based on GFP Accumulation", *Methods in Cell Biology*, 58:315-341 (1999).
Comack, B.P., et al, "FACS-Optimized Mutants of the Green Fluorescent Protein (GFP)", *Gene*, 173:33-38 (1996).

(Continued)

*Primary Examiner*—Christina Chan
*Assistant Examiner*—F. Pierre VanderVegt
(74) *Attorney, Agent, or Firm*—Douglas A. Petry

(57) ABSTRACT

Presented are intrinsically fluorescent, self-multimerizing MHC fusion proteins, and complexes assembled therefrom that are capable of detectably labeling antigen-specific T lymphocytes. Also presented are methods for labeling antigen-specific T lymphocytes with the intrinsically fluorescent complexes of the present invention, and methods, particularly flow cytometric methods, for detecting, enumerating, enriching, and depleting antigen specific T lymphocytes so labeled.

24 Claims, 13 Drawing Sheets

OTHER PUBLICATIONS

Matz, M.V., et al, "Fluoresent Proteins From Nonbioluminescent Anthozoa Species", *Nature Biotechnology*, 17:969-973 (1999).

Baird, G.S., et al, "Biochemistry, Mutagenesis, and Oligomerization of DsRed, a Red Fluorescent Protein from Coral", *Proceedings of the National Academy of Science USA*, 97:11984-11989 (2000).

Gross, L.A., et al, "The Structure of the Chromophore within DsRed a Red Fluorescent Protein From Coral", *Proceedings of the National Academy of Science USA*, 97:11990-11995 (2000).

Heikal, A.A., et al, "Molecular Spectroscopy and Dynamics of Intrinsically Fluorescent Proteins: Coral Red (dsRed) in Yellow (Citrine)" *Proceedings of the National Academy of Science USA*, 97:11996-12001 (2000).

Wall, M.A., et al, "The Structural Basis For Red Fluorescence in the Tetrameric GFP Homolog (DsRed)", *Nature Structural Biology*, 7:1133-1138 (2000).

* cited by examiner

INTRINSICALLY FLUORESCENT, SELF-MULTIMERIZING MHC FUSION PROTEINS AND COMPLEXES THEREOF

CROSS REFERENCE TO RELATED APPLICATION

This application claims the benefit of the filing date of U.S. provisional application Ser. No. 60/261,448, filed Jan. 12, 2001, the disclosure of which is incorporated herein by reference in its entirety.

FIELD OF THE INVENTION

The present invention relates to intrinsically fluorescent, self-multimerizing MHC fusion proteins and to complexes thereof, and to methods for using such complexes for the labeling, detection, enumeration, enrichment, isolation, depletion and activation of antigen specific T lymphocytes, particularly by flow cytometry.

BACKGROUND OF THE INVENTION

Soluble tetramers of major histocompatibility complex (MHC) proteins, charged with specific peptide antigen and fluorescently labeled ("MHC tetramers"), have in the past five years proven extraordinarily useful in the detection, enumeration, characterization and purification of antigen-specific T lymphocytes. Applications of MHC class I tetramers have recently been reviewed in Doherty et al., *Annu. Rev. Immunol.* 18:561–92 (2000); Ogg et al., *Immunol. Lett.* 66(1–3):77–80 (1999); Maini et al., *Immunol. Today* 20(6): 262–6 (1999); and Doherty, *Curr. Opin. Microbiol.* 1(4): 419–22 (1998). Applications of MHC class II tetramers are discussed in Reichstetter et al., *J. Immunol.* 165(12):6994–8 (2000); Kwok et al., *J. Immunol.* 164(8):4244–9 (2000); Liu et al., *Proc. Natl. Acad. Sci. USA* 97(26):14596–14601 (2000); Novak et al., *J. Clin. Invest.* 104(12):R63–7 (1999); Crawford et al., *Immunity* 8:675–682 (1998); and Kozono et al., *Nature* 369:151–154 (1994).

MHC tetramers bind to the T cell receptor ("TCR") of T lymphocytes in an antigen- and MHC-specific manner. See, e.g., Altman et al., *Science* 274:94 (1996) and U.S. Pat. No. 5,635,363.

Specificity of the staining reagent is conferred by both the MHC moiety and the peptide included within the tetrameric complex. Thus, tetramers comprising the extracellular domains of MHC class I α chain molecules, complexed to β2 microglobulin and charged with antigenic peptides of about 9 amino acids, will bind to class I-restricted, typically $CD8^+$, T cells specific for the charging peptide and MHC allele. Tetramers comprising four class II heterodimers— each heterodimer comprising the extracellular domains of MHC class II α and class II β chains—charged with antigenic peptides, will bind to class II-restricted, typically $CD4^+$, T cells in an antigen-specific and MHC-restricted fashion.

Avidity sufficient to allow stable binding to the T lymphocyte results from the multimerization of the MHC/peptide complex. In order to maintain self-tolerance, the natural affinity of TCR for MHC/peptide is low, too low to permit use of a univalent MHC/peptide complex as an immunological staining reagent. Matsui et al., *Science* 254: 1788–91 (1991); Matsui et al., *Proc. Natl. Acad. Sci. USA* 91:12862–6 (1994). Multimerization increases the avidity of the MHC/peptide complex for TCR sufficiently to permit stable binding. Typically, multimerization is achieved by enzymatic biotinylation of a BirA substrate peptide engineered into the MHC chain; the biotinylated MHC chain thereafter binds avidin or streptavidin with a 4:1 molar stoichiometry.

The MHC tetramer is rendered detectable by direct or indirect conjugation to a fluorophore. Typically, direct conjugation is accomplished by multimerizing the MHC/peptide molecules using a streptavidin or avidin molecule that has been prior-conjugated to a fluorophore. Such avidin and streptavidin proteins are commercially available from a variety of vendors (e.g., Becton Dickinson Immunocytometry Systems, San Jose, Calif., USA; Biomeda, Foster City, Calif., USA; Ancell Corp., Bayport, Minn. USA; Southern Biotechnology Assocs., Inc., Birmingham, Ala., USA). Indirect labeling can be performed using a fluorophore-conjugated antibody having specificity for the avidin/streptavidin moiety or for nonpolymorphic determinants of the multimerized MHC chain.

Although MHC tetramers have proven tremendously useful, certain aspects of their synthesis present problems.

Proper multimerization requires the controlled, stoichiometric, antecedent biotinylation of the MHC chain, and further requires the subsequent stoichiometric binding of the biotinylated chains to avidin or streptavidin. Inefficiency or imprecision at either or both of these steps affects yield and utility of the resulting tetrameric complex.

For example, inefficient biotinylation of the MHC chain—i.e., failure to incorporate at least one biotin per MHC molecule—will lead to decreased yield of tetramers. Inefficient removal of unconjugated biotin from the reaction products, with carry-over of unconjugated biotin molecules into the multimerization reaction, can saturate avidin molecules and also decrease tetramer yield.

Biotinylation of MHC molecules at multiple sites can reduce the avidity of resulting tetrameric complexes. Early attempts at multimerization using chemical biotinylation failed, possibly because multiple and random chemical modification of MHC molecules led to randomized, and often inactive, orientation of the MHC/peptide moieties in the multimerized complex. Although enzymatic biotinylation has improved control of the biotinylation process, enzymatic modification is itself subject to well known vicissitudes, including dependence upon enzyme concentration, substrate concentration, substrate accessibility, enzyme activity, and the like; multiple enzymatic biotinylation can mimic the poor avidity observed with the early, chemically-biotinylated, complexes.

Biotinylation at multiple sites of the MHC chain, combined with obligate use of an extrinsic multimerizing moiety, such as avidin, also makes possible the spurious generation of higher order multimers during the multimerization reaction. If even a small number of MHC/peptide subunits contain two or more biotins, cross-linking of the avidin/streptavidin moiety can occur. Such higher order multimers can exhibit decreased avidity due to steric hindrance, and can conversely, in other circumstances, lead to higher order complexes having increased avidity. Variations in avidity, whether decreases or increases from the mean, can lead to variations in staining intensity that are unrelated to TCR density or antigen affinity. Higher order multimers can also produce a more intense fluorescent signal, further leading to confounding variations in staining intensity.

Conversely, carry-over of unconjugated biotin molecules into the multimerization reaction can lead to partial saturation of avidin/streptavidin moieties with unconjugated biotin, leading to formation of multimeric complexes having fewer than four MHC/peptide subunits. Such lower order complexes can demonstrate lower avidity for TCR, leading to variations in staining intensity that are unrelated to TCR density or antigen/MHC affinity.

The requirement for a separate fluorophore conjugation step also presents opportunities for yield loss and for unintended variation in either avidity for TCR or fluorescence intensity, or both.

In a related approach, MHC/Ig chimeras, rather than tetramers of MHC, are used to label antigen-specific T lymphocytes. Dal Porto et al., *Proc. Natl. Acad. Sci. USA* 90:6671–6675 (1993); Greten et al., *Proc. Natl. Acad. Sci. USA* 95:7568–7573 (1998); Hamad et al., *J. Exp. Med.* 188:1633–1640 (1998); Schneck et al., U.S. Pat. Nos. 6,015,884 and 6,140,113.

In class I chimeras, the extracellular domains of MHC class I α chain are fused in-frame into the variable region of an IgG heavy chain. Under suitable oxidizing conditions, the heavy chain chimeras self-dimerize through disulfide bonds: dimerization confers avidity for TCR sufficient to permit use of the dimeric fusion protein as a T cell labeling reagent. As with MHC tetramers, the dimeric class I chimera molecule must be associated with β2 microglobulin and charged with specific antigenic peptide to permit recognition of antigen-specific T cells; unlike MHC tetramers, the MHC/Ig chimeric molecules must additionally be associated prior to use with Ig light chains.

In class II MHC/Ig chimeras, the extracellular domains of MHC class II α and β chains are separately fused to Ig heavy and light chain subunits, typically with the β subunit domains fused to IgG heavy chain and the class II α domains fused to Ig light, typically κ, chain. As with MHC tetramers, the class II chimeric molecule must be charged with specific antigenic peptide to permit recognition of antigen-specific T cells; for stability, antigenic peptide can be fused directly to the N terminus of the class II β subunit, Kozono et al., *Nature* 369:151–154 (1994); Liu et al., Proc. Natl. Acad. Sci. USA 97:14596–14601 (2000).

Labeling of the dimeric chimeras is typically accomplished using a fluorophore-conjugated, anti-Ig, secondary antibody.

The self-dimerizing chimeras obviate the biotinylation step and use of an extrinsic multimerizing moiety required by MHC chimeras, with their attendant problems. The dimeric chimeras also more readily permit post-synthesis loading with antigenic peptide.

However, the dimeric chimeras are not without problems of their own.

First, the dimeric valency can cause lower avidity for TCR than would be obtained using tetramers, reducing or abrogating the ability to label low affinity TCRs.

Second, the additional requirement for Ig light chain association—whether native Ig light chains, as in the class I chimeras, or recombinant Ig light chain fusion proteins, as in the class II chimeras—obligates the coexpression of multiple recombinant expression constructs in a single host cell or, in the case of class I chimeras, use of a host cell line that constitutively expresses Ig light chain.

Third, although self-dimerization obviates the biotinylation step and reliance upon an extrinsic multimerizing moiety of MHC tetramers, potentially improving yield of multimers of known valency (complexity), the dimers can dissociate under reducing conditions.

Additionally, each of the strategies for rendering the dimeric chimera fluorescently detectable presents difficulties.

For example, use of secondary antibodies for visualization can make simultaneous detection of multiple antigens more difficult; this can be a significant problem when, as is often the case, the population of antigen-specific T cells is small, obligating use of multiple parameters in order accurately to detect and enumerate the cells. Direct chemical conjugation of fluorophore to the chimera, an alternative to use of secondary antibodies, can interfere with or even abrogate affinity interactions of the chimera with its cognate TCR. Direct chemical conjugation can also lead to chimeric molecules having varying molar ratios of label, making flow cytometric or other fluorescence-based analyses more problematic.

Thus, there is a need for reagents that can be used to label T lymphocytes based upon their antigen (and MHC) specificity that have sufficient avidity to permit stable binding to T lymphocytes via interactions with surface TCR, but that do not require biotinylation and extrinsic multimerization; there is a concurrent need for antigen-specific T cell labeling reagents that can be rendered fluorescent without requiring use of secondary antibodies or direct chemical conjugation to fluorophore.

The substrate-independent, intrinsically fluorescent green fluorescent protein from *Aequorea victoria* ("GFP") has been used in the flow cytometric ("FACS") analysis of cells that express GFP, or GFP fusions, inside the cell. Reviewed in Galbraith et al., "Flow cytometric analysis and FACS sorting of cells based on GFP accumulation," *Methods Cell Biol.* 58:315–41 (1999). GFP variants having characteristics improved for flow cytometry have been described, U.S. Pat. Nos. 6,090,919 and 5,804,387; Cormack et al., *Gene* 173: 33–38 (1996). GFP and GFP variants have typically been used for internal labeling of cells, rather than for external labeling of cell surface structures.

A distant homologue of GFP, termed DsRed (also denominated drFP583), has recently been cloned from Discosoma coral, Matz et al., *Nature Biotechnol.* 17:969–973 (1999); vectors suitable for excision cloning, bacterial expression and mammalian expression of DsRed, alone or as a fusion protein, are now commercially available (Clontech Laboratories, Inc., Palo Alto, Calif., USA).

Native DsRed has an excitation (absorption) maximum of about 558 nm, and has an emission maximum of about 583 nm, a substantial red shift from the GFP emission maximum of about 509 nm. DsRed is thus readily excited by the standard 488 nm laser line routinely available in flow cytometers and has an emission spectrum readily distinguishable from autofluorescence background and from that of GFP, making DsRed a candidate for two-color flow cytometric applications in conjunction with GFP or FACS-optimized mutants of GFP.

Detailed studies of the structure and spectral properties of DsRed, Baird et al., *Proc. Natl. Acad. Sci. USA* 97:11984–11989(2000); Gross et al., *Proc. Natl. Acad. Sci. USA* 97:11990–11995 (2000); Heikal et al., *Proc. Natl. Acad. Sci. USA* 97:11996–12001 (2000); Wall et al., *Nature Structural Biol.* 7:1133–1138 (2000), however, have identified two characteristics that are said to militate against widespread use of DsRed in flow cytometric and other fluorescence analyses.

First, the red fluorescence of DsRed is slow to mature, requiring days to ripen fully from green to red, both in vitro and in vivo. A maturation time on the order of days will preclude attempts to use DsRed as a reporter of short-term gene expression or to track fusion proteins in organisms with short generation times or fast development. Baird et al., *Proc. Natl. Acad. Sci. USA* 97:11984–11989 (2000).

Second, DsRed appears to be an obligate, and self-multimerizing, tetramer. Baird et al., *Proc. Natl. Acad. Sci.*

USA 97:11984–11989 (2000); Wall et al., *Nature Structural Biol.* 7:1133–1138 (2000); Gross et al., *Proc. Natl. Acad. Sci. USA* 97:11990–11995 (2000). Although oligomerization may be irrelevant to use of DsRed as a simple reporter of gene expression, it will present serious problems in most potential applications where DsRed would be fused to a host protein to report on the trafficking or interactions of the latter. Furthermore, many proteins in signal transduction are activated by oligomerization; fusion to DsRed could cause constitutive signaling. For host proteins that are already oligomeric, fusion to DsRed could either cause clashes of stoichiometry, steric conflicts of quaternary structures, or cross-linking into massive aggregates.

Given these "major drawbacks," "[m]any potential cell biological applications of DsRed will require suppression of the tetramerization and acceleration of the maturation." Baird et al., *Proc. Natl. Acad. Sci. USA* 97:11984–11989 (2000). "For most biotechnological applications, both the slow maturation and oligomerization of DsRed are undesirable properties that must be addressed through systematic mutagenesis." Wall et al., *Nature Structural Biol.* 7:1133–1138 (2000). "The excellent brightness and stability of DsRed and many potential uses for a long-wavelength fluorescent protein provide ample justification for major efforts to remedy these remaining deficiencies." Gross et al., *Proc. Natl. Acad. Sci. USA* 97:11990–11995 (2000).

SUMMARY OF THE INVENTION

It is an object of the present invention to provide reagents that can be used to label T lymphocytes based upon their antigen (and MHC) specificity, that have sufficient avidity for T lymphocytes to permit stable binding to surface TCR without requiring biotinylation and use of an extrinsic multimerizing moiety, and that can be rendered fluorescent without requiring use of secondary antibodies or direct chemical conjugation to fluorophore. It is a further object of the invention to provide methods for labeling, detecting, enumerating, enriching, isolating, depleting, and activating antigen-specific T lymphocytes using such reagents.

These, and other needs in the art, are satisfied by the present invention, which exploits a property—tetramerization—that is said to be disadvantageous in the newly discovered, intrinsically fluorescent, self-multimerizing fluorophore, DsRed, and which, by use of the resulting tetramer as an extracellular, rather than intracellular label, is unaffected by the other property said in the art to be disadvantageous in DsRed, the slow maturation of its protein fluorophore after translation.

Thus, in a first aspect, the invention provides a recombinant fusion protein, comprising: a GFP-like chromophore; at least one multimerization domain; and an MHC peptide-presenting moiety. Functionally, the fusion protein comprises means for fluorescing, the fluorescing means encoded entirely within the amino acid sequence of the protein; means for multimerizing; and means that are capable of contributing to presentation of a peptide antigen to an MHC-restricted T lymphocyte.

In a preferred embodiment, the fusion protein of the present invention comprises, from N-terminus to C-terminus, contiguous α1, α2 and α3 domains drawn from a chosen MHC class I α subunit, followed in frame by substantially all of DsRed, which provides both the GFP-like fluorophore and two distinct multimerization domains. This preferred fusion protein spontaneously tetramerizes in solution.

When properly multimerized and charged with peptide, the fusion proteins of the present invention can be used, without further direct or indirect conjugation to an exogenous fluorophore, fluorescently to label T lymphocytes based upon their antigen (and MHC) specificity; the reagents of the present invention can thus be used in all methods for which MHC tetramers and MHC/Ig chimeric fusion proteins are presently used.

The fusion proteins of the present invention are typically produced by recombinant expression in host cells. Thus, in further aspects, the present invention includes nucleic acids that encode the above-described fusion proteins, and their complements, vectors comprising the nucleic acids, vectors for expressing the fusion proteins in host cells, host cells containing episomal or integrated vectors capable of expressing the fusion proteins of the present invention, and host cells containing any one of the nucleic acids, recombinant vector, expression vector, and fusion proteins of the present invention in one or more internal cellular compartments.

In other aspects, the present invention provides multimeric complexes that include, as plural subunits, the fusion proteins of the present invention. When properly complexed with appropriate soluble protein partners (e.g., β2 microglobulin for fusion proteins having an class I MHC peptide-presenting moiety) and charged with peptide, these intrinsically fluorescent multimeric complexes can be used to label T lymphocytes based upon their antigen (and MHC) specificity.

In the simplest such aspect, the invention provides an intrinsically fluorescent, multimeric protein complex, comprising: a plurality of subunits, the subunits having the quaternary formula in the complex of $(F)_n$, wherein F is a fusion protein according to the present invention and n is an integer greater than 1. Where the multimerization domain of the fusion protein is provided by DsRed or related fusion protein, the complex typically assembles with tetrameric valency (i.e., n=4).

In a related aspect, the invention further provides an intrinsically fluorescent, multimeric protein complex, comprising: a plurality of subunits, the subunits having the quaternary formula in the complex of $(F_1S_1)_n$, wherein F is a recombinant fusion protein according to the present invention, S is a soluble protein, and n is an integer greater than 1.

S is selected from the group consisting of β2 microglobulin, class II β MHC peptide-presenting soluble derivatives, and class II α MHC peptidepresenting soluble derivatives. S is β2 microglobulin when F includes a class I α MHC peptide-presenting moiety, S is a class II β MHC peptide-presenting soluble derivative when F includes a class II α MHC peptide-presenting moiety, and S is a class II α MHC peptide presenting soluble derivative when F includes a class II β MHC peptide-presenting moiety.

The multimeric complex, properly assembled with soluble protein (i.e., with $(F_1S_1)_n$ quaternary stoichiometry), can thereafter be charged with specific peptide, providing an intrinsically fluorescent reagent that is useful for detectable labeling of T lymphocytes based upon their antigen specificity.

Thus, in another aspect, the invention provides an intrinsically fluorescent, multimeric protein complex for labeling T lymphocytes based upon the specificity of their antigen receptor. The complex of this aspect of the invention comprises a plurality of subunits, the subunits having the quaternary formula in the complex of $(F_1S_1P_1)_n$, where F, as above, is a recombinant fusion protein of the present invention, S is a soluble protein as above-described, P is a peptide antigen, and n is an integer greater than 1.

The peptide antigen will be bound, as in MHC tetramers and MHC/Ig chimeras, by the MHC peptide-presenting domains of the multimeric complex of the present invention: in a class I MHC intrinsically fluorescent multimer, by the α1 and α2 domains of the class I α MHC peptide presenting moiety of the fusion protein subunit; in a class II multimer, by the α1 and β1 domains of the MHC peptide-presenting moiety and soluble derivatives of the complex.

Functionally, the intrinsically fluorescent, multimeric protein complex for labeling T lymphocytes according to the specificity of their antigen receptors, comprises: means for fluorescing, the means being encoded entirely within an amino acid sequence of at least one subunit of the multimeric complex; and means for binding to a T lymphocyte according to the specificity of its antigen receptor.

Once charged with a given peptide antigen, the intrinsically fluorescent complexes of the present invention can bind to T lymphocytes having antigen receptors that are specific for the given peptide and MHC peptide-presenting domains of the multimeric complex. Because the peptide antigens and MHC peptide-presenting domains of the complexes of the present invention can both be varied, the intrinsically fluorescent multimeric complexes of the present invention can be used, in general, fluorescently to label a near infinite variety of T lymphocytes based upon the antigen (and MHC) specificity of their antigen receptors.

It is, therefore, another aspect of the present invention to provide methods for using the multimeric complexes of the present invention detectably to label (stain) T lymphocytes based upon the specificity of their antigen receptors.

In a first embodiment, the method comprises contacting a T lymphocyte to be labeled with an intrinsically fluorescent multimeric complex of the present invention, the complex having peptide antigen and MHC peptide-presenting domains for which the antigen receptor of the T lymphocyte is specific, for a time and under conditions sufficient to permit detectable binding of the complex to the T lymphocyte.

Typically, the T lymphocytes to be labeled are present within a heterogeneous sample of cells, and the goal of labeling is to detect, and often to enumerate, the antigen specific T lymphocytes within this population.

Thus, in another aspect, the present invention provides methods for detecting, in a sample of cells, T lymphocytes that are specific for a chosen antigen. The method comprises contacting the sample with an intrinsically fluorescent multimeric complex according to the present invention, wherein the peptide antigen of the complex is the chosen antigen and the MHC presenting domains of the complex are those for which the T lymphocytes desired to be detected will be restricted, for a time and under conditions sufficient to permit detectable binding of the complex to T lymphocytes in the sample that are specific for the chosen antigen and MHC; and then detecting specific T lymphocytes in the sample by the fluorescence of the complex bound thereto. In a related aspect, the method further comprises enumerating the antigen-specific T lymphocytes so detected.

Depending upon the instrument used, detection of antigen-specific T lymphocytes can be coupled directly or indirectly to their sorting, thus providing, in other aspects of the invention, methods for enriching a sample in, and for depleting a sample of, T lymphocytes that are specific for a chosen antigen.

In general, the methods of this aspect of the invention comprise contacting the sample with an intrinsically fluorescent multimeric complex of the present invention, wherein the peptide antigen of the complex is the chosen antigen and the MHC presenting domains of the complex are those for which the T lymphocytes desired to be enriched or depleted will be restricted, for a time and under conditions sufficient to permit detectable binding of the complex to T lymphocytes in the sample that are specific for the chosen antigen and MHC. After binding, labeled T lymphocytes are enriched or depleted based upon the fluorescence of the complex bound thereto.

Such methods are conveniently performed using a fluorescence activated cell sorter: sorting based at least in part upon fluorescence from the multimeric complex of the present invention directly depletes the sample from which the cells are removed and enriches the aliquot into which the cells are placed.

The multimeric complex compositions of the present invention can usefully be provided in the form of kits that facilitate the practice of the methods of the present invention. Thus, in another aspect, the present invention provides kits comprising the intrinsically fluorescent multimeric complexes of the present invention.

In one series of embodiments, the kits of the present invention include, as separate compositions, an intrinsically fluorescent $(F_1S_1)_n$ multimer of the present invention, and an antigenic peptide; as noted above, the choice of peptide will depend upon the specificity desired for the labeling reagent. In another series of embodiments, the multimer is prior-charged with peptide. Optionally, but advantageously, included in either of these series of kits as separate compositions can be any of fluorophore-conjugated antibodies to pan-T or T cell subsetting antigens, fluorophore-conjugated antibodies specific for T cell activation antigens, and red cell lysing reagents.

BRIEF DESCRIPTION OF THE DRAWINGS

The above and other objects and advantages of the present invention will be apparent upon consideration of the following detailed description taken in conjunction with the accompanying drawings, in which like characters refer to like parts throughout, and in which.

DETAILED DESCRIPTION OF THE INVENTION

Definitions

Figure 1:
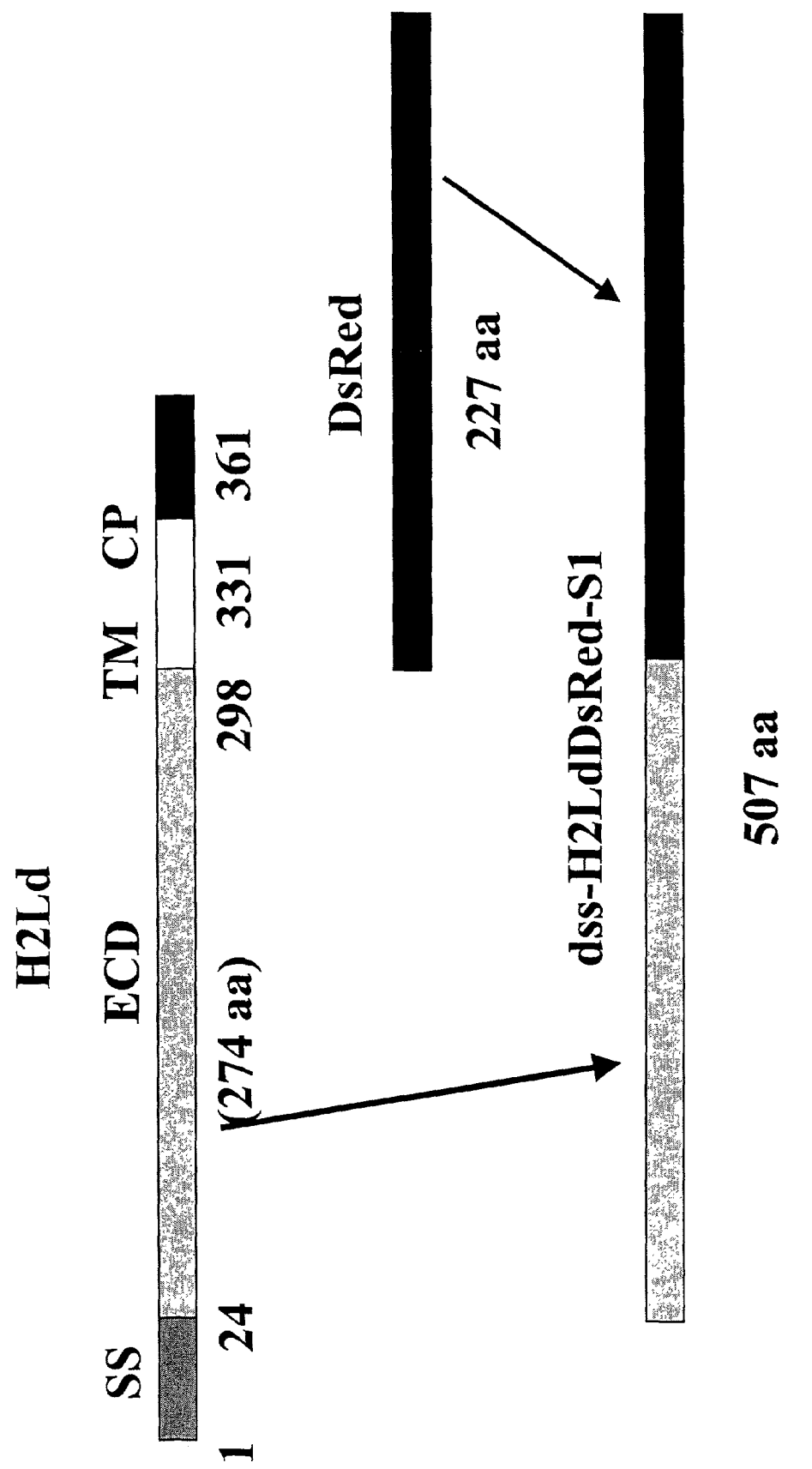
FIG. 1 schematizes construction of an H2Ld MHC class I-DsRed recombinant fusion construct according to the present invention.

As used herein, the terms set forth with particularity below have the following definitions. If not otherwise defined in this section, all terms used herein have the meaning commonly understood by a person skilled in the arts to which this invention belongs.

"GFP-like chromophore" means an intrinsically fluorescent protein moiety comprising an 11-stranded $\beta$-barrel ($\beta$-can) with a central $\alpha$-helix, the central $\alpha$-helix having a conjugated $\pi$-resonance system that includes two aromatic ring systems and the bridge between them. By "intrinsically fluorescent" is meant that the GFP-like chromophore is entirely encoded by its amino acid sequence and can fluoresce without requirement for cofactor or substrate.

"MHC peptide-presenting moiety", "MHC peptide-presenting soluble derivative", and "MHC peptide-presenting domains" all refer to portions of a major histocompatibility complex protein chain that lack a transmembrane domain (and are thus "soluble") and that can participate in presentation of peptide antigen to a T cell receptor. The term "MHC peptide-presenting moiety" is used when the soluble MHC portion is included within a fusion protein; the variant "MHC peptide-presenting soluble derivative" is used when the protein is expressed unfused; the phrase "MHC peptide-presenting domains" is used generically to both contexts.

Class I $\alpha$ MHC peptide-presenting domains include substantially all of the $\alpha 1$, $\alpha 2$ and $\alpha 3$ domains of an MHC class I molecule; by "substantially all" is meant that deletions therefrom and substitutions thereof are permissible only when they do not interfere with ability of the $\alpha 3$ domain to form an intradomain disulfide bond or the ability of $\alpha 1$ and $\alpha 2$ domains to form alpha helices properly positioned to bind peptide.

Class II $\alpha$ MHC peptide-presenting domains include substantially all of the $\alpha 1$ and $\alpha 2$ domains of an MHC class II $\alpha$ chain molecule; by "substantially all" is meant that deletions therefrom or substitutions thereof are permissible only when they do not interfere with the ability of $\alpha 2$ domain to form intrachain disulfide bonds or with the ability of the $\alpha 1$ domain to form a peptide binding $\alpha$ helix.

Class II $\beta$ MHC peptide-presenting domains include substantially all of the $\beta 1$ and $\beta 2$ domains of an MHC class II $\beta$ chain molecule. By "substantially all" is meant that deletions therefrom or substitutions thereof are permissible only when they do not interfere with the ability of the $\beta 2$ domain to form intrachain disulfide bonds or of the $\beta 1$ domain to form peptide binding $\alpha$ helix.

Fusion Proteins

In a first aspect, the present invention provides a recombinant fusion protein that, when properly multimerized and charged with peptide, can be used, without further direct or indirect conjugation to an exogenous fluorophore, fluorescently to label T lymphocytes based upon their antigen (and MHC) specificity; the reagents of the present invention can thus be used in all methods for which MHC tetramers and MHC/Ig chimeric fusion proteins are presently used, including peptide antigen-specific activation of T-cells.

The fusion protein of the present invention comprises a GFP-like chromophore, at least one multimerization domain, and an MHC peptide-presenting moiety.

A GFP-like chromophore is an intrinsically fluorescent protein moiety. By "intrinsically fluorescent" is meant that the GFP-like chromophore is entirely encoded by its amino acid sequence and can fluoresce without requirement for cofactor or substrate.

Structurally, the GFP-like chromophore comprises an 11-stranded $\beta$-barrel ($\beta$-can) with a central $\alpha$-helix, the central $\alpha$-helix having a conjugated $\pi$-resonance system that includes two aromatic ring systems and the bridge between them. The $\pi$-resonance system is created by autocatalytic cyclization among amino acids; cyclization proceeds through an imidazolinone intermediate, with subsequent dehydrogenation by molecular oxygen at the $C\alpha$-$C\beta$ bond of a participating tyrosine.

The GFP-like chromophore can be selected from GFP-like chromophores found in naturally occurring proteins, such as *A. victoria* GFP (GenBank accession number AAA27721), *Renilla reniformis* GFP, FP583 (GenBank accession no. AF168419) (DsRed), FP593 (AF272711), FP483 (AF168420), FP484 (AF168424), FP595 (AF246709), FP486 (AF168421), FP538 (AF168423), and FP506 (AF168422), and need include only so much of the native protein as is needed to retain the chromophore's intrinsic fluorescence. Methods for determining the minimal domain required for fluorescence are known in the art. Li et al.,"Deletions of the *Aequorea victoria* Green Fluorescent Protein Define the Minimal Domain Required for Fluorescence," *J. Biol. Chem.* 272:28545–28549 (1997).

Alternatively, the GFP-like chromophore can be selected from GFP-like chromophores modified from those found in nature. Typically, such modifications are made to improve recombinant production in heterologous expression systems (with or without change in protein sequence), to alter the excitation and/or emission spectra of the native protein, to facilitate purification, to facilitate or as a consequence of cloning, or are a fortuitous consequence of research investigation.

The methods for engineering such modified GFP-like chromophores and testing them for fluorescence activity, both alone and as part of protein fusions, are well-known in the art. Early results of these efforts are reviewed in Heim et al., *Curr. Biol.* 6:178–182 (1996), incorporated herein by reference in its entirety; a more recent review, with tabulation of useful mutations, is found in Palm et al., "Spectral Variants of Green Fluorescent Protein," in *Green Fluorescent Proteins*, Conn (ed.), *Methods Enzymol.* vol. 302, pp. 378–394 (1999), incorporated herein by reference in its entirety. A variety of such modified chromophores are now commercially available and can readily be used in the fusion proteins of the present invention.

For example, EGFP ("enhanced GFP"), Cormack et al., *Gene* 173:33–38 (1996); U.S. Pat. Nos. 6,090,919 and 5,804,387, is a red-shifted, human codon-optimized variant of GFP that has been engineered for brighter fluorescence, higher expression in mammalian cells, and for an excitation spectrum optimized for use in flow cytometers. EGFP can usefully contribute a GFP-like chromophore to the fusion proteins of the present invention. A variety of EGFP vectors, both plasmid and viral, are available commercially (Clontech Labs, Palo Alto, Calif., USA), including vectors for bacterial expression, vectors for N-terminal protein fusion expression, vectors for expression of C-terminal protein fusions, and for bicistronic expression.

Toward the other end of the emission spectrum, EBFP ("enhanced blue fluorescent protein") and BFP2 contain four amino acid substitutions that shift the emission from green to blue, enhance the brightness of fluorescence and improve solubility of the protein, Heim et al., *Curr. Biol.* 6:178–182 (1996); Cormack et al., *Gene* 173:33–38 (1996). EBFP is optimized for expression in mammalian cells whereas BFP2, which retains the original jellyfish codons, can be expressed in bacteria; as is further discussed below, the host cell of production does not affect the utility of the resulting fusion protein. The GFP-like chromophores from EBFP and BFP2 can usefully be included in the fusion proteins of the present invention, and vectors containing these blue-shifted variants are available from Clontech Labs (Palo Alto, Calif., USA).

Analogously, EYFP ("enhanced yellow fluorescent protein"), also available from Clontech Labs, contains four amino acid substitutions, different from EBFP, Ormö et al., *Science* 273:1392–1395 (1996), that shift the emission from green to yellowish-green. Citrine, an improved yellow fluorescent protein mutant, is described in Heikal et al., *Proc. Natl. Acad. Sci. USA* 97:11996–12001 (2000). ECFP ("enhanced cyan fluorescent protein") (clontech Labs, Palo Alto, Calif., USA) contains six amino acid substitutions, one of which shifts the emission spectrum from green to cyan. Heim et al., *Curr. Biol.* 6:178–182 (1996); Miyawaki et al., *Nature* 388:882–887 (1997). The GFP-like chromophore of each of these GFP variants can usefully be included in the fusion proteins of the present invention.

The GFP-like chromophore can also be drawn from other modified GFPs, including those described in U.S. Pat. Nos. 6,124,128; 6,096,865; 6,090,919; 6,066,476; 6,054,321; 6,027,881; 5,968,750; 5,874,304; 5,804,387; 5,777,079; 5,741,668; and 5,625,048, the disclosures of which are incorporated herein by reference in their entireties.

The fusion proteins of the present invention further include at least one multimerization domain. If plural multimerization domains are present, the domains need not be identical to one another. The multimerization domains can function either to effect homomultimerization or heteromultimerization, and can contribute to noncovalent or covalent association of the individual subunits.

For example, the multimerization domain can usefully be drawn from existing, self-dimerizing, MHC/Ig chimeras, which are further described in Dal Porto et al., *Proc. Natl. Acad. Sci. USA* 90:6671–6675 (1993); Greten et al., *Proc. Natl. Acad. Sci. USA* 95:7568–7573 (1998); Hamad et al., *J. Exp. Med.* 188:1633–1640 (1998); Schneck et al., U.S. Pat. Nos. 6,015,884 and 6,140,113, the disclosures of which are incorporated herein by reference in their entireties. The multimerizing moiety of these chimeras includes an IgG Fc region, which is capable of disulfide-linked homodimerization.

Other protein multimerization domains are well known, and include, for example, leucine zipper domains.

The multimerization domain(s) can also usefully be provided by the same protein that provides the GFP-like chromophore.

DsRed exists as an obligate tetramer, even in dilute solution, and has not been observed to monomerize without protein denaturation, Gross et al., *Proc. Natl. Acad. Sci. USA* 97:11990–11995 (2000); Wall et al., *Nature Structural Biol.* 7:1133–1138 (2000), a property that has been viewed in the art as disadvantageous and warranting interventional ablation. In the present invention, this disadvantageous property proves surprisingly useful, allowing DsRed to provide both the GFP-like chromophore and the multimerization domains to the fusion protein of the present invention; with such multimerization domains, the fusion proteins of the present invention readily assemble into soluble MHC/peptide complexes with the tetrameric valency, and thus avidity characteristics, of known MHC tetramers.

DsRed contains two dissimilar multimerization domains, both of which appear necessary to its tetramerization. The smaller domain shows characteristics typical of many high-affinity protein-protein interaction surfaces, and is perhaps specifically tuned for homooligomeric interaction; the larger interface is dramatically different in chemical character, and has characteristics observed at oligomerization interfaces that seem to require broader tuning of substrate specificity.

The two multimerization domains of DsRed can advantageously be used in the fusion proteins of the present invention in association with the native DsRed GFP-like chromophore, providing the excitation (absorption) maximum of about 558 nm, emission maximum of about 583 nm, strong resistance to photobleaching and strong pH independence of the native DsRed protein.

Alternatively, the multimerization domains of DsRed can be used with GFP-like chromophores modified from the native DsRed chromophore. For example, the green-only DsRed mutant K83R (lysine to arginine at residue 83, numbering as in Baird et al., *Proc. Natl. Acad. Sci. USA* 97:11984–11989 (2000)) fails to mature to red fluorescence, yet tetramerizes, and thus will prove useful in the fusion proteins of the present invention, providing tetramers with emission spectrum readily distinguishable from those of tetramers composed of fusions using the native DsRed fluorophore. Conversely, DsRed mutant K83M has a 602 nm emission maximum, with relatively little residual green fluorescence, Baird et al., *Proc. Natl. Acad. Sci. USA* 97:11984–11989 (2000)), and thus will provide further spectral separation from green- and yellow-emitting fluorophores. Other DsRed chromophore mutants can readily be created, expressed, and screened for spectral and oligomerization characteristics, essentially as described in Baird et al., *Proc. Natl. Acad. Sci. USA* 97:11984–11989 (2000).

Additionally, although DsRed is only 22% identical in sequence to GFP, the overall structure of the chromophore is strikingly conserved as between these distant homologues. Thus, the chromophore from *A. victoria* GFP and its many known variants, including EGFP, EYFP, EBFP, and Citrine, can readily be substituted for the DsRed chromophore, altering the spectral properties of the protein while retaining the DsRed multimerization domains. This can advantageously be done by engineering into existing DsRed vectors restriction sites that flank the DsRed chromophore and that are suitable for excision and in-frame replacement of the DsRed GFP-like chromophore by cassettes containing the sequence coding for other GFP-like chromophores.

Such DsRed/GFP chimeras are thus suitable for and can advantageously be used for inclusion in the fusion proteins of the present invention. As further discussed below, fusion proteins of the present invention that have the DsRed multimerizing moieties and differing GFP-like chromophores can be assembled into heteromeric tetramers in which the respective chromophores participate as donor and acceptor in fluorescence resonance energy transfer ("FRET") reactions.

Multimerization domains can also be provided by fluorescent protein homologues of DsRed or *A. victoria* GFP.

For example, *Renilla reniformis* GFP is believed to be an obligate dimer. Ward, in *Green Fluorescent Protein: Properties, Applications, and Protocols*, eds. Chalfie & Kain (Wiley, N.Y.) (1998). The *Renilla* GFP multimerization domain can usefully be used in the fusion proteins of the present invention to permit self-assembly of complexes with the dimeric valency, and thus avidity characteristics, of existing MHC/Ig chimeras.

Further, Wall et al., *Nature Structural Biol.* 7:1133–1138 (2000), report that oligomerization appears to be a general property of the DsRed-like fluorescent proteins, such as FP593, FP483, FP484, FP595, FP486, FP538 and FP506. Thus, each of these fluorescent proteins can usefully contribute one or more multimerization domains to the fusion protein of the present invention. As with use of the DsRed multimerization domains, the fusion protein of the present invention can include the GFP-like chromophore of the fluorescent protein contributing the multimerization domain(s), a mutational variant thereof, or, alternatively, can include the GFP-like chromophore of another, homologous, fluorescent protein or a variant thereof.

The fusion proteins of the present invention further include an MHC peptide-presenting moiety.

The MHC peptide-presenting moiety is a soluble portion of a major histocompatibility complex protein chain that is capable of participating in, but may not itself be sufficient for, antigen presentation to a T cell receptor.

The MHC peptide-presenting moiety can be derived from MHC class I, MHC class II, or nonclassical MHC molecules.

If derived from class I, the MHC peptide-presenting moiety will be derived from the MHC class I α chain and will include the α1, α2 and α3 domains; permissible deletions therefrom or substitutions thereof cannot interfere with ability of the α3 domain to form an intradomain disulfide bond or the ability of α1 and α2 domains to form alpha helices properly positioned to bind peptide.

If derived from class II, the MHC peptide-presenting moiety of the fusion protein of the present invention will be derived from either the MHC class II α or β chain; multimeric complexes of the present invention, useful for detecting class II restricted antigen-specific T cell labeling, will, as further discussed below, include both fusion proteins having a class II α- and a class II β-derived MHC peptide-presenting moiety.

If derived from class II α chain, the MHC peptide presenting moiety of the fusion protein of the present invention will include α1 and α2 domains; permissible deletions therefrom or substitutions thereof must not interfere with ability of α2 domain to form intrachain disulfide bonds or with the ability of the α1 domain to form a peptide binding α helix. If derived from class II β chain, the MHC peptide presenting moiety of the fusion protein of the present invention will include β1 and β2 domains; permissible deletions therefrom or substitutions thereof must not interfere with ability of the β2 domain to form intrachain disulfide bonds or of the β1 domain to form peptide binding α helix.

If derived from a nonclassical MHC molecule, the domains to be included will depend upon whether the molecule bears greater sequence homology to classical class I or to class II MHC molecules.

The MHC peptide-presenting moiety will lack the transmembrane region of its respective parent MHC molecule; typically, the MHC peptide-presenting moiety will also lack the cytoplasmic region of the respective MHC molecule.

The MHC peptide presenting moiety of the fusion protein of the present invention can be derived from the MHC molecules of any mammalian or avian species. For use in multimeric complexes for labeling of antigen-specific T cells, the MHC peptide presenting moiety will advantageously be drawn from the MHC molecules of the species whose T cells are to be detected.

Thus, the MHC peptide presenting moiety of the fusion protein of the present invention can advantageously be derived from human and other primate MHC molecules, from rodent, particularly mouse, rat, hamster, and guinea pig MHC, and from rabbit, bovine, canine, feline, and equine MHC. The MHC peptide presenting moiety of the fusion protein of the present invention can thus usefully be drawn from the human class II subunits HLA-DPα, HLA-DPβ, HLA-DQα, HLA-DQβ, HLA-DRα and HLA-DRβ, the human class I subunits HLA-A, HLA-B, HLA-C, murine class II subunits I-Aα, I-Aβ, I-Eα, I-Eβ, and murine class I subunits H-2K, H-2D, and H-2L.

The MHC peptide presenting moiety of the fusion protein of the present invention can be substantially the same as, and can be identical to, the MHC-derived portions of MHC tetramers, further described in Doherty et al., *Annu. Rev. Immunol.* 18:561–92 (2000); Ogg et al., *Immunol. Lett.* 66(1–3):77–80 (1999); Maini et al., *Immunol. Today* 20(6): 262–6 (1999); Doherty, *Curr. Opin. Microbiol.* 1(4):419–22 (1998); Reichstetter et al., *J. Immunol.* 165(12):6994–8 (2000); Kwok et al., *J. Immunol.* 164(8):4244–9 (2000); Liu et al., *Proc. Natl. Acad. Sci. USA* 97(26):14596–14601 (2000); Novak et al., *J. Clin. Invest.* 104(12):R63–7 (1999); Crawford et al., *Immunity* 8:675–682 (1998); Kozono et al., *Nature* 369:151–154 (1994); Altman et al., *Science* 274:94 (1996); and Altman et al., U.S. Pat. No. 5,635,363.

The MHC peptide presenting moiety of the fusion protein of the present invention can be substantially the same as, and can be identical to, the MHC-derived portions of MHC/Ig chimeras, further described in Dal Porto et al., *Proc. Natl. Acad. Sci. USA* 90:6671–6675 (1993); Greten et al., *Proc. Natl. Acad. Sci. USA* 95:7568–7573 (1998); Hamad et al., *J. Exp. Med.* 188:1633–1640 (1998); Schneck et al., U.S. Pat. Nos. 6,015,884 and 6,140,113, the disclosures of all of which are incorporated herein by reference in their entireties.

Other MHC molecules that can contribute MHC peptide-presenting moieties can be found in *Sequences of Proteins of Immunological Interest*, Kabat et al., (eds.), 5th ed., U.S. Dept. of Health and Human Services, Public Health Service, National Institutes of Health (1991), the disclosure of which is incorporated herein by reference in its entirety, and The Kabat Database of Sequences of Proteins of Immunological Interest, http:// immuno.bme.nwu.edu/, further described in Johnson et al., *Nucl. Acids Res.* 29: 205–206 (2001).

Typically, but not invariably, the MHC peptide presenting moiety will be located N-terminal to both the GFP-like chromophore and the multimerization domains of the fusion protein of the present invention. The relative position of the chromophore and multimerization domains, in turn, will depend in large part upon their source.

For example, where the multimerization domain (and perhaps also the MHC peptide presenting moiety) is drawn from an existing MHC/Ig chimera, the GFP-like chromophore is advantageously fused to the C terminus of the existing MHC/Ig chimera. As another example, where the GFP-like chromophore and multimerization domains are drawn from a single escent protein, such as DsRed, the relative positions will be determined by their relative positions in the native protein. Relative positioning of the multimerization domain(s) and GFP-like chromophore may also depend upon cloning considerations, the solutions to which are well within the knowledge of the skilled molecular biologist.

In a preferred embodiment, the fusion protein of the present invention comprises, from N-terminus to C-terminus, contiguous α1, α2 and α3 domains drawn from a chosen MHC class I α subunit, followed in frame by substantially all of DsRed, which provides both the GFP-like chromophore and two distinct multimerization domains. The fusion protein spontaneously tetramerizes in solution. The resulting tetramers can be used, after complexing with β2-microglobulin and charging with peptide, and without further labeling, in all uses for which classic class I MHC tetramers and class I MHC/Ig chimeras have proven useful.

The fusion protein of the present invention can also usefully include, N-terminal to the MHC-presenting moiety, the antigenic peptide itself; this is particularly useful in fusions that include an MHC class II β subunit peptide presenting moiety. Kozono et al., *Nature* 369:151–154 (1994); Liu et al., Proc. Natl. Acad. Sci. USA 97:14596–14601 (2000), incorporated herein by reference in their entireties.

The fusion protein can also advantageously include, at either N-terminus or C-terminus, a sequence useful for purification. Where present directly adjacent to the MHC peptide-presenting moiety, this fused tag is preferentially selectively removable.

For example, the fusion protein can include a polyhistidine tag, permitting purification by immobilized metal affinity chromatography, for example using NiNTA resin (Qiagen Inc., Valencia, Calif., USA) or TALON™ resin (cobalt immobilized affinity chromatography medium, Clontech Labs, Palo Alto, Calif., USA). As another example, the fusion protein can include a chitin-binding tag and self-excising intein, permitting chitin-based purification with self-removal of the fused tag (IMPACT™ system, New England Biolabs, Inc., Beverley, Mass., USA). Alternatively, the fusion protein can include a calmodulin-binding peptide tag, permitting purification by calmodulin affinity resin (Stratagene, La Jolla, Calif., USA), or a specifically excisable fragment of the biotin carboxylase carrier protein, permitting purification of in vivo biotinylated protein using an avidin resin and subsequent tag removal (Promega, Madison, Wis., USA).

In alternative embodiments, the fusion protein can also advantageously include a protein spacer fused in frame between the MHC-presenting moiety and any of the GFP-like chromophore and multimerization domain or domains; the spacer provides a flexible link between the MHC-presenting moiety and other components of the fusion protein. The linker sequence may appear once, or as multiple tandem repeats of the same sequence. Suitable amino acid sequences that will provide a flexible link between the MHC-presenting moiety and DsRed, and techniques for inserting such a spacer into the fusion construct, are within the knowledge of the skilled artisan.

Nucleic Acids, Vectors, and Host Cells

The fusion proteins of the present invention are typically produced by recombinant expression in host cells. Thus, in further aspects, the present invention includes nucleic acids that encode the above-described fusion proteins, vectors comprising the nucleic acids, vectors for expressing the fusion proteins in host cells, host cells containing episomal or integrated vectors capable of expressing the fusion proteins of the present invention, and host cells containing the fusion proteins of the present invention in one or more internal cellular compartments.

The nucleic acids of the present invention comprise sequences that encode the fusion protein or that are complementary in sequence to those that encode the fusion protein. The nucleic acids (or respective complements thereof) can encode the fusion protein as a single open reading frame or, when the encoding nucleic acid is to be used for eukaryotic expression of the fusion protein, can encode the fusion protein as a plurality of exons with intervening introns.

Figure 11:
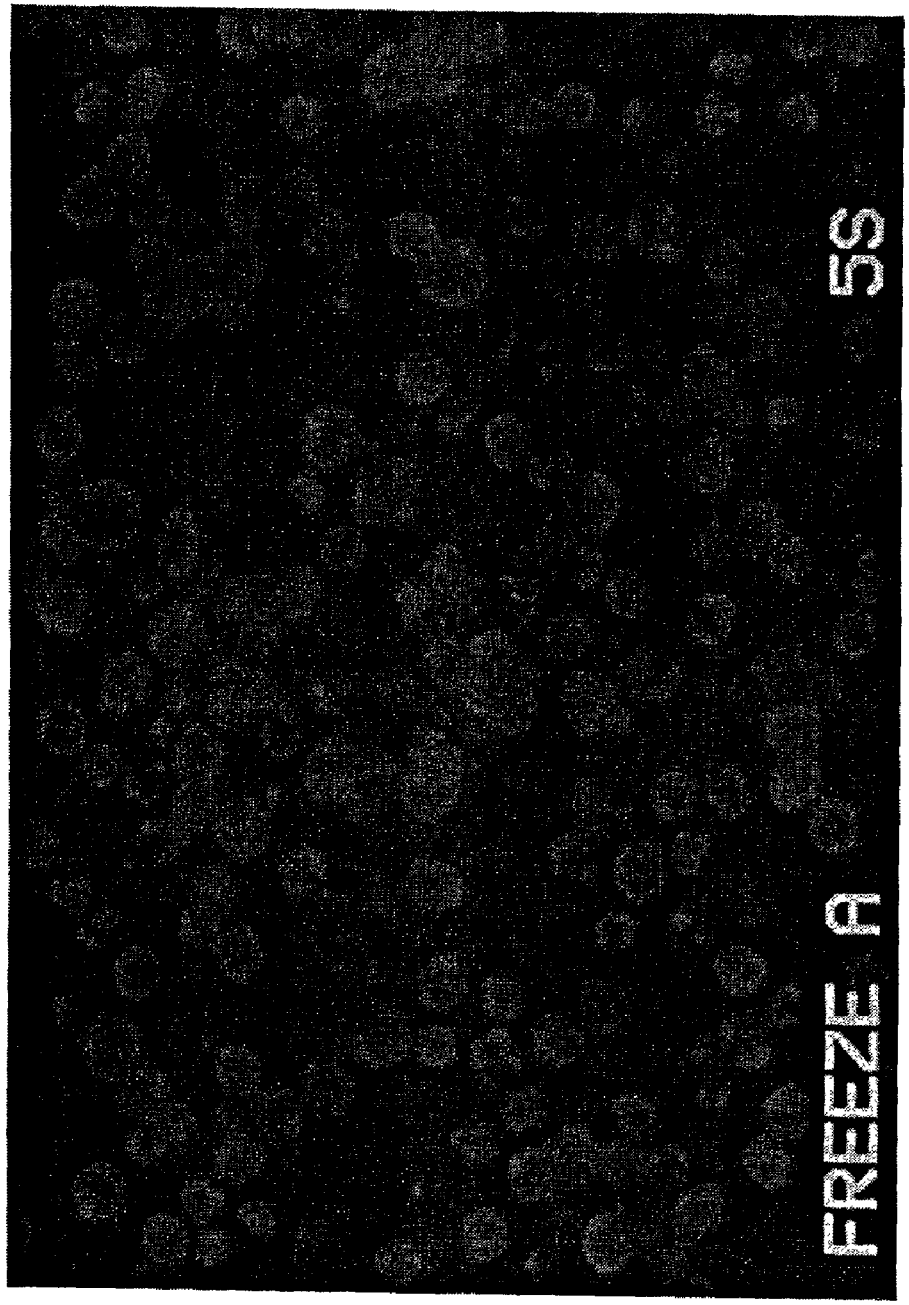
FIG. 11 is a photograph by fluorescent microscopy using a rhodamine filter of Sf9 cells infected with the H2Ld-DsRed recombinant baculovirus grown three days in culture post-infection, showing red fluorescence.
Figure 13:
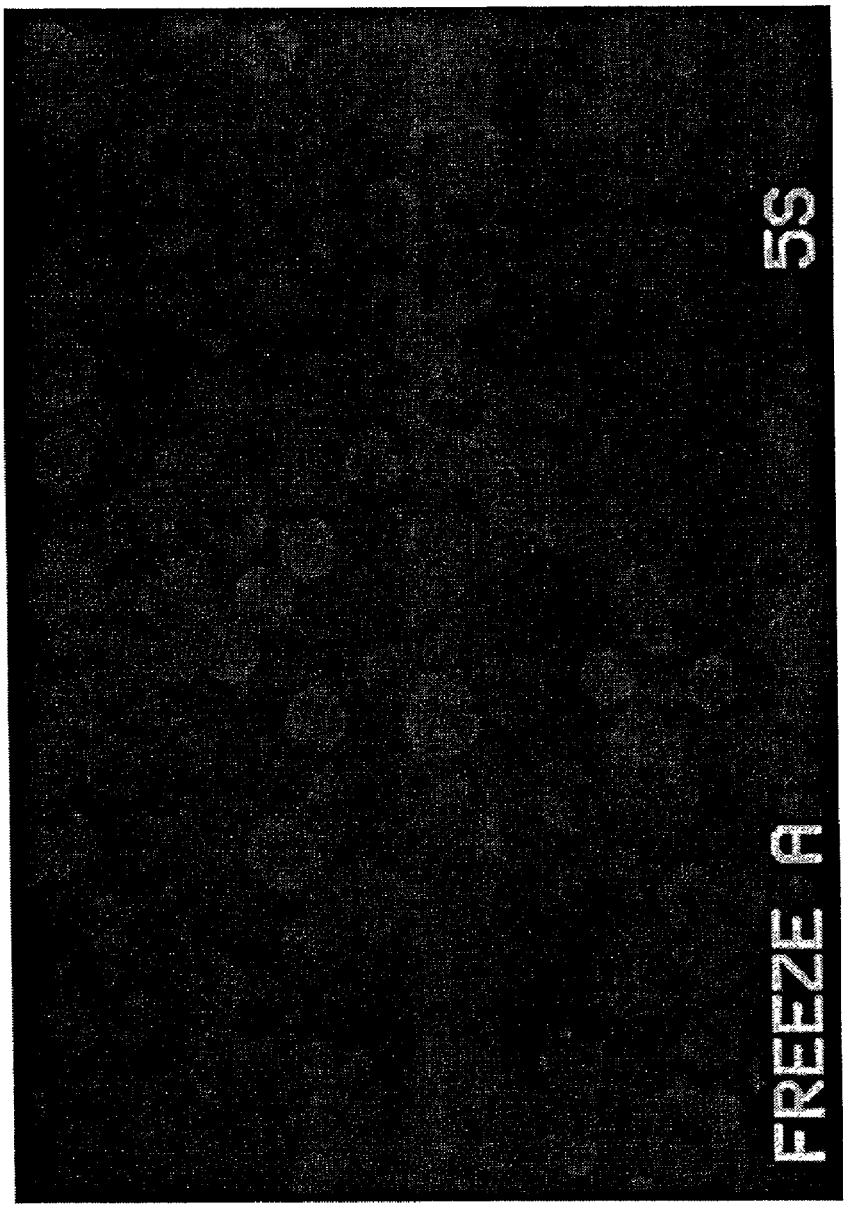
FIG. 13 is a photograph by fluorescent microscopy using a rhodamine filter of Tni cells infected with the H2Ld-DsRed recombinant baculovirus grown three days in culture post-infection, showing red fluorescence.

The nucleic acids of the present invention can be in the form of DNA, typically but not invariably double-stranded, or in the form of RNA. Where the DNA encodes the fusion protein as a plurality of exons, the RNA transcript can exist in both unspliced form, containing the introns, and one or more spliced forms. The nucleic acids of the present invention can also include nonnative nucleotides, alternative internucleotide linkages, or both, typically when the nucleic acids are used as probes rather than for expression of the fusion protein. Probes are useful for confirming transfection of the nucleic acid into host cells and transcription thereof, although fluorescence emission can often itself be used as a measure of transfection and expression efficiency, as indicated by FIGS. 11 and 13.

The nucleic acids of the present invention can be engineered to use codons optimized for expression in various types of host cells, providing nucleic acid molecules of differing nucleic acid sequence that encode the same fusion protein. The nucleic acids of the present invention can be in isolated and purified form, e.g. in the form of purified plasmid preparation, and can also be in the form of nucleic acids integrated into one or more chromosomes of a prokaryotic or eukaryotic host cell.

As further demonstrated in the Examples below, the nucleic acids of the present invention can usefully be incorporated into vectors that permit propagation and amplification of the nucleic acids of the present invention in one or more types of eukaryotic and prokaryotic host cells, including mammalian cells, particularly human and rodent cells, insect cells, yeast cells, and bacterial cells, particularly *E. coli* cells, providing nucleic acids for probe construction, further recombinant manipulation, such as mutagenesis, and for cloning into further vectors.

The vectors of the present invention can be plasmid, viral, or combination or variant thereof (e.g., phagemid, cosmid), can be an artificial chromosome (e.g., BAC, YAC, HAC), or can be any other type of cloning and/or expression vector known in the art.

Vectors can be constructed de novo, using techniques well known in the art, as are described, inter alia, in Sambrook et al., *Molecular Cloning: A Laboratory Manual,* 3rd ed., Cold Spring Harbor Laboratory Press (2000); Ausubel et al. (eds.), *Short Protocols in Molecular Biology: A Compendium of Methods from Current Protocols in Molecular Biology,* 4th ed., John Wiley & Sons (1999); Jones et al.

(eds.), *Vectors: Cloning Applications: Essential Techniques* (Essential Techniques Series), John Wiley & Son Ltd. (1998); Cid-Arregui et al. (eds.), *Viral Vectors: Basic Science and Gene Therapy*, Eaton Publishing Company/Bio Techniques Books Division (2000), the disclosures of which are incorporated herein by reference in their entireties.

Alternatively, the vectors of the present invention can usefully and advantageously be modified from or include relevant portions of vectors presently used to propagate and/or express DsRed and/or other fluorescent proteins, MHC tetramers, and/or MHC/Ig chimeras.

For example, a variety of DsRed vectors useful as starting material for constructing the vectors of the present invention are available commercially from Clontech Labs (Palo Alto, Calif. USA). pDsRed Vector is a prokaryotic expression vector containing the native DsRed sequence flanked by multiple cloning sites; the DsRed coding sequence can be excised by restriction digest or retrieved by PCR amplification. pDsRed1-1 encodes a DsRed variant having a valine insertion at position 2, with 144 silent changes to optimize expression in mammalian cells. pDsRed1-N1 readily permits mammalian expression of fusions to DsRed N-terminus; pDsRed1-C1 readily permits mammalian expression of fusions to the DsRed C-terminus.

For example, MHC tetramer expression vectors useful as starting material for constructing the vectors of the present invention are described in Doherty et al., *Annu. Rev. Immunol.* 18:561–92 (2000); Ogg et al., *Immunol. Lett.* 66(1–3): 77–80 (1999); Maini et al., *Immunol. Today* 20(6):262–6 (1999); Doherty, *Curr. Opin. Microbiol.* 1(4):419–22 (1998); Reichstetter et al., *J. Immunol.* 165(12):6994–8 (2000); Kwok et al., *J. Immunol.* 164(8):4244–9 (2000); Liu et al., *Proc. Natl. Acad. Sci. USA* 97(26):14596–14601 (2000); Novak et al., *J. Clin. Invest.* 104(12):R63–7 (1999); Crawford et al., *Immunity* 8:675–682 (1998); Kozono et al., *Nature* 369:151–154 (1994); Altman et al., *Science* 274:94 (1996); and Altman et al., U.S. Pat. No. 5,635,363, the disclosures of which are incorporated herein by reference in their entireties.

For example, vectors for expression of MHC/Ig chimeras that are useful as starting material for constructing the vectors of the present invention are further described in Dal Porto et al., *Proc. Natl. Acad. Sci. USA* 90:6671–6675 (1993); Greten et al., *Proc. Natl. Acad. Sci. USA* 95:7568–7573 (1998); Hamad et al., *J. Exp. Med.* 188: 1633–1640 (1998); Schneck et al., U.S. Pat. Nos. 6,015,884 and 6,140,113, the disclosures of all of which are incorporated herein by reference in their entireties.

Particularly useful among vectors of the present invention are those can be used for expressing the fusion proteins of the present invention in host cells. Details of expression vector construction are well known in the art and need not be reviewed here. In general terms, however, the expression vectors of the present invention include those that replicate episomally within the host cell and those that are integrated into one or more locations of the host cell genome; expression of the fusion protein from the vector can be constitutive or inducible, and the expressed fusion protein can be retained within the cell or secreted.

The present invention further includes host cells containing the nucleic acids, typically the vectors, including expression vectors, of the present invention, either episomally or integrated at one or more locations in the host cell chromosome. Where integrated, the expression vector is usefully present in multiple copies, which increased copy number can be effected by amplification techniques well known in the art (see, e.g., Axel et al., U.S. Pat. No. 4,399,216, the disclosure of which is incorporated herein by reference). Where the host cells include expression vectors of the present invention, the host cells typically further include the fusion proteins of the present invention in one or more cellular compartments.

The host cells of the present invention can contain a plurality of vectors, including expression vectors, of the present invention; the plurality of vectors can respectively encode a plurality of different fusion proteins, thus permitting expression within the cell of heteromeric multimers. As will be further described, such heteromeric multimers can usefully include fusion proteins having identical MHC antigen-presenting moiety and multimerization domains but different GFP-like chromophores.

Host cells useful for propagation of the nucleic acids of the present invention include bacterial cells, particularly *E. coli* cells, and eukaryotic cells.

Host cells useful for recombinant production of the fusion proteins of the present invention include all types of cells typically used for recombinant expression, including both prokaryotic and eukaryotic cells, the latter including human, rodent, insect, and yeast cells.

Insect cells, such as Sf9 and Tni cells, present certain advantages for expression of the fusion proteins of the present invention, including high yield (see, e.g., FIGS. 11 and 13) and likely a low load of endogenous peptide spuriously loaded on the nascent multimers during synthesis. Rodent myeloma cells present certain advantages for expression, particularly where the fusion protein includes most, or all, of an Ig/MHC chimera, fused to a GFP-like chromophore; notable among such advantages is concurrent production of Ig light chain.

Where the fusion protein to be expressed includes an MHC peptide-presenting moiety from a class I MHC molecule, the host cells of the present invention can also usefully and concurrently express β2 microglobulin, either endogenously or through expression of a second recombinant construct.

Where the expressed fusion protein is capable of multimerizing in the intracellular milieu, the host cells typically further include such multimers.

Multimeric Complexes

In another aspect, the present invention provides multimeric complexes that include, as plural subunits, fusion proteins of the present invention. When properly complexed with appropriate soluble protein partners (e.g., β2 microglobulin for fusion proteins having a class I MHC peptide-presenting moiety) and charged with peptide, these intrinsically fluorescent multimeric complexes can be used to label T lymphocytes based upon their antigen (and MHC) specificity.

In its simplest form, the multimeric complex of the present invention comprises a multimer of the fusion proteins of the present invention, giving the complex a quaternary formula of $(F)_n$, where F is a fusion protein as above-described and n is an integer greater than 1.

Multimerization is driven and mediated by the multimerization domains of the fusion protein. Where the multimerization domain(s) of the fusion protein subunits are drawn from DsRed, variants thereof, or related fluorescent proteins, the fusion protein subunits will typically assemble predominantly into tetramers (n=4), with possible formation of weakly associated octamers (n=8). Where the multimerization domain(s) of the fusion protein subunits are drawn instead from *Renilla* GFP or from IgG Fc regions, the fusion protein subunits will typically assemble predominantly into dimers (n=2).

If the fusion protein subunits are expressed in eukaryotic cells, such as rodent myeloma cells or insect cells, the fusion protein subunits will typically self-assemble within the cell into complexes of the expected valency. If the fusion protein subunits are instead expressed in prokaryotic cells, such as *E. coli*, the subunits will typically assemble only after denaturation (e.g., in 8M urea) and renaturation, as is well known in the MHC tetramer art.

The resulting multimeric complex is intrinsically fluorescent, due to the presence of GFP-like chromophores in each of the participating subunits. The spectral qualities of the complex will be dictated not only by the spectral properties of the individual GFP-like chromophores present within the complex, but by their collective interaction as well.

A particularly significant interaction among GFP-like chromophores is fluorescence resonance energy transfer ("FRET").

The multimeric complex of the present invention can include fusion protein subunits having different GFP-like chromophores, so long as the fusion protein subunits remain able to multimerize through their respective multimerization domains. Typically, but not invariably, the fusion protein subunits of such heteromultimeric complexes will all have the same MHC peptide-presenting moieties. Where the different GFPlike chromophores have suitable spectral overlap, their proximity and relative angular displacement within the multimeric complex can permit fluorescence resonance energy transfer between the different GFP-like chromophores.

It is known, for example, that the DsRed chromophore can be used as an acceptor in a fluorescence resonance energy transfer (FRET) pair with enhanced green fluorescent protein (EGFP) or yellow fluorescent protein (YFP) mutants. Heikal et al., *Proc. Natl. Acad. Sci. USA* 97:11996–12001 (2000). Furthermore, fluorescence resonance energy transfer among monomers in the native DsRed tetramer has been reported. Thus, where the multimeric complex of the present invention includes both a fusion protein subunit having a DsRed GFP-like chromophore and a fusion protein subunit having an EGFP GFP-like chromophore, the spectral properties of the complex can reflect fluorescence resonance energy transfer between EGFP and DsRed chromophores, allowing the complex to be excited more readily at the EGFP absorption maximum than would have been possible with a homotetramer having only the DsRed chromophores.

As noted above, fluorescence resonance energy transfer can occur between and among GFP-like chromophores present in the subunits of the multimeric complexes of the instant invention. FRET can additionally and usefully be established between the GFP-like chromophore of one or more of the subunits of the complex and a fluorophore associated therewith.

Techniques for associating a fluorophore with a subunit of the multimeric complex, so as to support FRET—by conjugating, linking, or adding the fluorophore to the subunit, or otherwise modifying a subunit with the fluorophore—are within the knowledge of the skilled artisan.

Depending on the absorption and emission spectra of the fluorophore that is associated with a particular type of GFP-like chromophore, either the fluorophore or the GFP-like chromophore can serve as the fluorescence energy donor or acceptor.

Fluorophores useful as FRET donors or acceptors when associated with one or more subunits of the multimeric complex of the present invention include: cyanine 3 (e.g., Cy3, Cy3B); cyanine 5 (e.g., Cy5, Cy5Q); cyanine 5.5; cyanine 7 (e.g., Cy7Q); SYBR® Green (Molecular Probes); fluorescein and fluorescein derivatives (e.g., 6-carboxyfluoroscein); rhodamine and rhodamine derivatives (e.g., dichlororhodamine, dR110, dR6G, dTAMRA, dROX); allophycocyanin and allophycocyanin derivatives (e.g., GT5 APC); R-phycoerythrin; B-phycoerythrin; Y-phycoerythrin; R-phycocyanin; C-phycocyanin; Texas Red®; and proteinaceous fluorophores, e.g., PerCP.

According to a preferred embodiment, the GFP-like chromophore serves as the FRET donor and the fluorophore serves as the FRET acceptor. In this manner, stimulatory light energy of the appropriate wavelength is absorbed by the GFP-like chromophore and is transferred intramolecularly to the fluorophore, which then fluorescently emits the energy at a different, longer wavelength.

This arrangement can usefully accelerate the rate of fluorescent light emission.

The rate of fluorescent decay of some GFP-like fluorophores, after light stimulation, is relatively slow. For example, the energized DsRed chromophore decays to its ground state by fluorescent emission over a time period of microseconds. In contrast, intramolecular energy transfer by FRET between a GFP-like chromophore, such as DsRed, and an associated fluorophore typically occurs in nanoseconds. As a result, fluorescent emission by the fluorophore may be faster than fluorescent emission by the GFP-like fluorophore. The effect of this difference in the rate of fluorescent energy emission is that within a brief, predetermined time period, fluorescent light emission by the fluorophore, coupled by FRET to the GFP-like chromophore is greater, and the signal appears brighter. In contrast, within the same time period, fluorescent light emission by the GFP-like chromophore, unassisted by FRET and a fluorophore is lower, and the signal appears dimmer.

Increasing the rate of fluorescent emission of GFP-like chromophores, such as by the FRET-mediated mechanism described above, can be particularly advantageous when using flow cytometry. FRET-mediated acceleration of fluorescence emission by associating a fluorophore with a GFP-like chromophore will also be desirable in any other application in which signal acquisition must be made quickly or signal maximized.

In general, suitable selection of GFP-like chromophores to be included in the fusion protein subunits multimerized in the complex (and optionally FRET donors and acceptors conjugated thereto) will allow fine tuning of the spectral characteristics of the complex. One important utility of such tuning is to match the absorption and emission characteristics of the complex to the excitation and detection parameters of the analytical instrument, typically a flow cytometer. Conversely, as is further discussed below, lasers, filter sets, and detectors can be chosen that match the absorption and emission characteristics of the multimeric complex.

For detectable labeling of antigen-specific T lymphocytes, the multimeric complex of the present invention will further include soluble protein partners and peptides. The above-described $(F)_n$ complexes are useful intermediates, however, in the preparation of these labeling reagents, and will usefully be sold to end users desiring themselves to complete formation of the complex.

Thus, in a further aspect, the invention includes intrinsically fluorescent, multimeric protein complexes comprising a plurality of subunits, the subunits having the quaternary formula in the complex of $(F_1S_1)_n$, where F, as above described, is a recombinant fusion protein of the present invention, S is a soluble protein, and n is an integer greater than 1.

S is selected from the group consisting of β2 microglobulin, class II β MHC peptide-presenting soluble derivatives, and class II α MHC peptide-presenting soluble derivatives: S is β2 microglobulin when F includes a class I α MHC peptide-presenting moiety; S is a class II β MHC peptide-presenting soluble derivative when F includes a class II α MHC peptide-presenting moiety; and S is a class II α MHC peptide-presenting soluble derivative when F includes a class II β MHC peptide-presenting moiety.

Typically, the soluble protein is derived from the same taxonomic species as provides the MHC peptide-presenting moiety of the fusion protein in the complex. For example, when the fusion protein includes MHC class I α domains from mouse, the soluble β2 microglobulin used in the multimeric complex will be murine β2 microglobulin. For example, where the fusion protein includes human HLA-DQα domains, the MHC peptide-presenting soluble derivative included within the complex will include human class II β domains, such as HLA-DQβ domains.

The soluble protein can be coexpressed with the fusion protein subunits in a single host cell, facilitating self-assembly of the $(F_1S_1)_n$ complex within the cell, or can be added to a prior-assembled complex having the quaternary formula $F_n$. When the fusion protein subunits of the multimeric complex include a class II MHC peptide-presenting moiety, the class II MHC peptide-presenting soluble derivative will most typically be coexpressed therewith, particularly when expression of the fusion protein is effected in eukaryotic cells; when the fusion protein subunits of the multimeric complex include a class I α MHC peptide-presenting moiety, the β2 microglobulin soluble protein can readily be coexpressed therewith or added after assembly of the $(F)_n$ multimer. Coexpression of β2 microglobulin in eukaryotic cells can result either from expression from a recombinant construct or, depending upon the choice of host cell, from endogenous expression by the host cell itself.

The multimeric complex, properly assembled with soluble protein, can thereafter be charged with specific peptide, providing an intrinsically fluorescent reagent that is useful for detectable labeling (and, in other methods, activation) of T lymphocytes based upon their antigen specificity.

It would be understood that the complex above-described—that is, inclusive of fusion protein and soluble protein subunits but lacking peptide antigen—can be charged with an enormous variety of peptide antigens, each peptide conferring its own specificity on the completed labeling reagent. The above-described $(F_1S_1)_n$ complex is thus extremely useful in the preparation of labeling reagents; and often, the intrinsically fluorescent complexes of the present invention will usefully be sold to the end-user in such form to permit the end-user to charge the complex with the peptide antigen of his or her choice.

Charged with peptide antigen, the multimeric complex is directly usable to label T lymphocytes based upon the antigen- (and MHC-) specificity of their T cell receptors. Thus, in another aspect, the invention provides an intrinsically fluorescent, multimeric protein complex for labeling T lymphocytes, the complex comprising a plurality of subunits, the subunits having the quaternary formula in the complex of $(F_1S_1P_1)_n$, where F, as above, is a recombinant fusion protein of the present invention, S is a soluble protein as above-described, P is a peptide antigen, and n is an integer greater than 1.

The peptide antigen will be bound, as in MHC tetramers and MHC/Ig chimeras, by the MHC peptide-presenting domains of the multimeric complex of the present invention: in a class I MHC intrinsically fluorescent multimer, by the α1 and α2 domains of the class I α MHC peptide presenting moiety of the fusion protein subunit; in a class II multimer, by the α1 and β1 domains of the MHC peptide-presenting moiety and soluble derivatives of the complex.

Where the complex of the present invention is a class I multimer, the peptide antigen will typically be no fewer than about 5, more typically no fewer than about 6, more typically no fewer than about 7, often no fewer than about 8 or 9 amino acids in length, and will typically be no more than about 15, typically no more than about 14, more typically no more than about 13, 12, or 11, and often no more than about 10, or 9 amino acids in length.

As is well known in the immunologic arts, the antigenic peptides can have a wider length range when complexed to MHC class II. Thus, for charging class II multimers, the peptides will typically be no fewer than about 8, typically no fewer than about 9, 10, 11 or 12 amino acids in length, and will typically be no more than about 30, typically no more than about 25, typically no more than about 19, 18, 17, or 16 amino acids in length, often no more than about 12 amino acids in length. And as noted above, for class II multimers the peptide can be covalently fused to the N terminus of the MHC peptide-presenting moiety or soluble derivative, Kozono et al., Nature 369:151–154 (1994); Liu et al., Proc. Natl. Acad. Sci. USA 97:14596–14601 (2000), rather than non-covalently associated Peptides will typically be substantially pure and of uniform sequence, such as can advantageously be prepared by chemical synthesis optionally followed by further purification, as, e.g., by HPLC. However, for some uses, a collection of peptides—e.g., a collection of peptides useful for vaccinating against CMV, as is described in WO 00/75180, the disclosure of which is incorporated herein by reference in its entirety—can be used to charge the intrinsically fluorescent multimers of the present invention. In this latter case, a population of multimers is created that will collectively label T lymphocytes that recognize any of the charging peptides. For such purposes, the peptides can be advantageously be created by endoproteolytic digest of a native protein, such as a viral protein.

Peptides can include nonnative amino acids and nonnative linkages, where such nonnative amino acids and/or nonnative linkages do not interfere with the ability of the intrinsically fluorescent complex to label T lymphocytes. For example, nonnative amino acids and/or linkages can be used to assess the T cell response to immunization with a protein or peptide that includes such nonnative amino acids or linkages, or to detect T lymphocytes specific for the peptide in its native form where the nonnative amino acids and/or linkages do not affect the three dimensional structure of the peptide.

Where the multimeric complexes of the present invention are prepared by recombinant expression in eukaryotic cells, particularly mammalian cells, the multimer may spuriously include peptides endogenous to the host cell. Although expression in insect cells can decrease the amount of endogenous peptide loading, a certain percentage of peptide binding sites can nonetheless be occupied prior to intentional loading. In such cases, peptide charging of the multimeric complexes will include some degree of peptide exchange.

Exchange can be facilitated at higher temperatures, such as 37° C., and by using higher concentrations of charging peptide. Where the concentration of peptide used for charging is high, and indeed at any peptide concentration, dialysis can optionally be performed after charging is completed to reduce the concentration of unbound peptide.

The sequence of the charging peptide will be dictated by the use to which the labeling reagent is to be put. For example, to detect the antigen-specific CD8+ T cell response to viral infection or viral vaccination, a peptide sequence derived from viral protein will be used to charge a class I intrinsically fluorescent multimer; to detect the presence of autoimmune T lymphocytes associated with multiple sclerosis, a peptide derived from myelin basic protein can be used to charge a class I or class II intrinsically fluorescent multimer.

As noted, particularly useful are peptides from viruses, such as HIV (human immunodeficiency virus), SIV (simian immunodeficiency virus), CMV (cytomegalovirus), HBV (hepatitis B virus), HCV (hepatitis C virus), HSV (herpes simplex virus), EBV (Epstein Barr virus), and HPV (human papilloma virus). Also useful are bacterial peptides, such as peptides from mycobacteria, including TB. Another class of peptides advantageously used are peptides derived from cancer-related antigens, particularly cancer antigens used in potential cancer vaccines, notably vaccines against melanoma, prostate cancer, and breast cancer.

Peptides used in the multimeric complexes of the present invention can also be selected on the basis of their mimicry of non-peptide structures, such as carbohydrates, Luo et al., *J. Biol. Chem.* 275(21):16146–54 (2000); O et al., *Biochem. Biophys. Res. Commun.* 5;268(1):106–11 (2000); Grothaus et al., *Vaccine* 18(13):1253–63 (2000); and Phalipon et al., *Eur. J. Immunol.* 27(10):2620–5 (1997).

The multimeric complexes of the present invention, with or without associated peptide (i.e., with either of quaternary formulas $(F_1S_1)_n$ or $(F_1S_1P_1)_n$), can usefully be provided as an aqueous composition, typically including buffers, salts and/or stabilizers, e.g., phosphate buffered saline with gelatin and 0.1% sodium azide, and it is thus another aspect of the present invention to provide such compositions. Alternatively, the complexes can be provided as nonaqueous, lyophilized compositions.

Methods of Use

Once charged with a given peptide antigen, the intrinsically fluorescent complexes of the present invention can bind to T lymphocytes having antigen receptors that are specific for the given peptide and MHC peptide-presenting domains of the multimeric complex. Because the peptide antigens and MHC peptide-presenting domains of the complexes of the present invention can both be varied, the intrinsically fluorescent multimeric complexes of the present invention can be used, in general, fluorescently to label a near infinite variety of T lymphocytes based upon the antigen (and MHC) specificity of their antigen receptors.

It is, therefore, another aspect of the present invention to provide methods for using the multimeric complexes of the present invention detectably to label (stain) T lymphocytes based upon the specificity of their antigen receptors.

In a first embodiment, the method comprises contacting a T lymphocyte to be labeled with an intrinsically fluorescent multimeric complex of the present invention, the complex having peptide antigen and MHC peptide-presenting domains for which the antigen receptor of the T lymphocyte is specific, for a time and under conditions sufficient to permit detectable binding of the complex to the T lymphocyte.

In the present context, a T lymphocyte is said to be specific for a peptide antigen when the affinity of its antigen receptor (TCR) for the peptide antigen in the MHC context of the complex is sufficiently high as to confer upon the complex as a whole avidity for the T lymphocyte that is sufficient to achieve detectable binding of the complex to TCRs on the lymphocyte surface.

Often, the peptide antigen(s) for which the T lymphocyte is said to be specific by this definition will also be capable of stimulating cytokine expression by the T lymphocyte; such a functional response is not, however, required, since the utility of the multimeric complexes of the present invention, as for MHC tetramers, is not limited to labeling and identification of functionally responsive T lymphocytes. Furthermore, by this definition it is not impossible for a single T lymphocyte, having a single αβ or γδ TCR species on its surface, to be said to be specific for a plurality of (typically closely related) peptide antigens. In such cases, the TCR will typically have greater affinity for one of the peptides than for the others.

Conditions and times adequate for such labeling can conveniently be adapted from those used in the art for staining T lymphocytes with MHC tetramers or MHC/Ig fusions.

For example, Altman et al., *Science* 274:94–96 (1996) stain 200,000 cytotoxic lymphocytes with MHC tetramers by incubation at 4° C. for one hour at a concentration of tetramer of approximately 0.5 mg/ml; the NIAID Tetramer facility presently recommends staining at each of 4° C., room temperature, and 37°, for 15–60 minutes, to optimize signal to noise ratio, with decreasing incubation times used for higher temperatures; Greten et al., *Proc. Natl. Acad. Sci. USA* 95:7568–7573 (1998) stain $1 \times 10^6$ peripheral blood mononuclear cells at 4° with 3 µg of MHC class I MHC/Ig chimera.

Thus, T lymphocytes can conveniently be labeled with the intrinsically fluorescent multimeric complexes in the methods of the present invention using at least about 0.1 µg, typically at least about 0.25 µg, more typically at least about 1 µg, 2 µg, 3 µg, 4 µg, or even at least about 5 µg of multimer to label about $10^4$, $10^5$, $10^6$ or even $10^7$ peripheral blood mononuclear cells using an incubation of 15–60 minutes at a temperature between 4° C. and 37° C.

Starting with these broad, exemplary, guidelines, those skilled in labeling T lymphocytes using MHC tetramers, MHC/Ig fusions, and fluorophore-conjugated antibodies will readily be able to determine optimal labeling conditions. Variables that affect the amount of multimeric reagent to be used and the temperature and duration of staining include those related to the T lymphocytes—the number of T lymphocytes in the sample that are specific for the peptide antigen (and MHC) of the complex, the total number of cells in the sample, the form of the cellular sample (e.g., whole blood, whole blood after red blood cell lysis, Ficoll-purified peripheral blood mononuclear cell (PBMC) fraction)—and those related to the multimeric complex, including the stoichiometry and molecular weight of the labeling complex, the identity of the peptide antigen, and the choice of MHC alleles included in the complex.

To optimize labeling conditions, labeling reactions can readily be performed using parallel aliquots of the cellular sample to be labeled using a single species of multimeric complex and varying labeling conditions (e.g., temperature, duration, complex concentration, cell number, cell concentration, cellular purity). Negative controls can include labeling reactions using no multimer, using multimer lacking peptide, and/or using multimer containing MHC peptide-presenting domains and/or peptide antigen that will not be recognized by T lymphocytes in the cellular sample. Effectiveness of labeling can be readily determined for each aliquot by flow cytometric enumeration of T lymphocytes in the sample that bind the fluorescent complex. As is well known in the flow cytometric arts, the labeled cells can be washed prior to flow cytometry to remove unbound complex from the cells and medium. All of these optimizing techniques and approaches are routine, and routinely performed by technicians, in the flow cytometric arts.

Typically, the T lymphocytes to be labeled are present within a heterogeneous sample of cells, and the goal of labeling is to detect, and often to enumerate, the antigen specific T lymphocytes within this population.

Thus, in another aspect, the present invention provides methods for detecting, in a sample of cells, T lymphocytes that are specific for a chosen antigen. The method comprises contacting the sample with an intrinsically fluorescent multimeric complex according to the present invention, wherein the peptide antigen of the complex is the chosen antigen and the MHC presenting domains of the complex are those for which the T lymphocytes desired to be detected will be restricted, for a time and under conditions sufficient to permit detectable binding of the complex to T lymphocytes in the sample that are specific for the chosen antigen and MHC; and then detecting specific T lymphocytes in the sample by the fluorescence of the complex bound thereto.

The detection of cell-bound fluorescence is typically performed using a flow cytometer, such as a FACSVantage™, FACSVantage™ SE, or FACSCalibur™ flow cytometer (Becton Dickinson Immunocytometry Systems, San Jose, Calif., USA). The lasers chosen for excitation will be determined by the absorption spectrum of the multimeric complex and of any additional fluorophores desired to be detected concurrently in the sample. For example, if the multimeric complex has the spectral characteristics of native DsRed—e.g., a homotetramer in which the fusion protein subunits all have the native DsRed GFP-like chromophore—a standard argon ion laser with 488 nm line can be used for excitation. For detection, the filter sets and detector types will be chosen according to the emission spectrum of the multimeric complex and of any additional fluorophores desired to be detected in the sample. For example, if the multimeric complex has the spectral characteristics of native DsRed, with emission maximum at about 583 nm, fluorescence emission from the complex can be detected in the FL2 channel using a PE setup.

Alternatively, cell-bound complex fluorescence can be detected using a microvolume fluorimeter, such as the IMAGN 2000 (Becton Dickinson Immunocytometry Systems, San Jose, Calif., USA). Applications of microvolume fluorimetry to, and conditions for, characterization of blood cell are described, inter alia, in Seghatchian et al., *Transfus. Sci.* 22(1–2):77–9 (2000); Glencross et al., *Clin. Lab. Haematol.* 21(6):391–5 (1999); and Read et al., *J. Hematother.* 6(4):291–301 (1997).

Alternatively, cell-bound complex fluorescence can be detected using a laser scanning cytometer (Compucyte Corp., Cambridge, Mass., USA).

Cell-bound fluorescence of the multimeric complex can also be detected directly on a microscope slide, using conditions essentially as described in Skinner et al., "Cutting edge: In situ tetramer staining of antigen-specific T cells in tissues," *J. Immunol.* 165(2):613–7 (2000).

The T lymphocyte-containing sample can be a whole blood sample, typically a peripheral venous blood specimen drawn directly into an anticoagulant collection tube (e.g., EDTA-containing or heparin-containing Vacutainer™ tube, Becton Dickinson Vacutainer Systems, Franklin Lakes, N.J., USA).

Advantageously, the T lymphocyte-containing sample can also be a whole blood sample that has been treated before detection with a red blood cell (RBC) lysing agent as is described, inter alia, in Chang et al., U.S. Pat. Nos. 4,902,613 and 4,654,312; lysing agents are well known in the art and are available commercially from a number of vendors (FACS™ Lysing Solution, Becton Dickinson Immunocytometry Systems, San Jose, Calif., USA; Cal-Lyse™ Lysing Solution, Caltag Labs, Burlingame, Calif., USA; No-Wash Lysing Solution, Beckman Coulter, Inc., Fullerton, Calif.). The sample can optionally be washed after RBC lysis and before detection.

The sample within which T lymphocytes are desired to be detected according to the methods of the present invention can also be a peripheral blood fraction, advantageously a mononuclear cell (PBMC) fraction. PBMCs can be prepared according to any of the well-known art-accepted techniques, among which are centrifugation through a density medium, such as Ficoll-Paque (Amersham Pharmacia Biotech, Piscataway, N.J., USA) and centrifugation directly in a specially designed cell preparation blood collection tube (e.g., Vacutainer™ CPT™ Cell Preparation Tube, Becton Dickinson, Franklin Lakes, N.J., USA).

The sample within which T lymphocytes are desired to be detected according to the methods of the present invention can also advantageously be a sample enriched in T lymphocytes. For example, the sample can be a sample of cultured lymphocytes (as from a clonal cell line or multiclonal culture), lymphocytes extracted or eluted from a tissue having lymphocytic infiltrate (e.g., tumor infiltrating lymphocytes extracted from a tumor biopsy and optionally expanded in culture), lymphocytes drawn from lymphatics or thymus, or lymphocytes obtained after at least a first round of fluorescence-activated cell sorting.

In another embodiment, the method further comprises enumerating the antigen-specific T lymphocytes so detected. Enumeration can conveniently be expressed in the form of a total cell count, percentage of antigen-specific T lymphocytes among cells assayed (either total, mononuclear, or T lymphocytic), or percentage of antigen-specific lymphocytes in a T cell subset.

For several of these metrics, it is necessary additionally to quantitate the total number of T lymphocytes within the sample as a whole, or the total number of T lymphocytes of a particular subset within the sample as a whole.

Thus, in other embodiments, the method of the present invention further comprises contacting the sample with at least one fluorophore-conjugated antibody, the antibody selected from the group consisting of pan-T antibodies and T cell subsetting antibodies, and then detecting fluorescence concurrently from the multimeric fluorescent complex and from the fluorophore-conjgated antibodies. By "pan-T antibody" is intended an antibody that recognizes a surface marker or epitope present on all, or substantially all, T lymphocytes. By "T cell subsetting antibody" is meant an antibody that binds to a surface marker present on fewer than all T lymphocytes.

Antibodies usefully used in this embodiment include antibodies specific for CD3, CD4, CD8, CD45RO, CD45RA, and CD27. As would be understood, the antibodies would typically be specific for the marker as expressed by the taxonomic species (human, mouse, rat, etc.) whose T lymphocytes are being detected, or would be cross-reactive therewith.

As is well known in the flow cytometric arts, fluorescence emission from the pan-T and/or T lymphocyte subsetting antibodies can be used for any or all of triggering data acquisition, live gating, or gating prior-acquired data.

It is often advantageous in the methods of the present invention to acquire a large number of events since, in many samples, antigen-specific T lymphocytes occur infrequently. In addition, it is possible at times to improve the signal to noise ratio for detecting such rare antigen-specific T cell events by triggering or gating on fluorescence from antibodies specific for T lymphocyte activation antigens.

Thus, in another embodiment, the method further comprises contacting the sample with at least one fluorophore-conjugated antibody specific for a T cell activation antigen, and then detecting fluorescence concurrently from the multimeric fluorescent complex and from the fluorophore-conjugated antibodies. The antibodies can usefully be specific for an activation antigen selected from the group consisting of CD69, CD25, CD71 and MHC class II (for labeling human T lymphocytes, advantageously HLA-DR).

Advantageously, the antibodies used in these embodiments of the methods of the present invention will be prior-conjugated directly to a fluorophore, typically a fluorophore whose emission is flow cytometrically distinguishable from that of the intrinsically fluorescent multimeric T cell labeling complex and from that of other fluorophores concurrently used in the method. Fluorophores can usefully be selected from the group consisting of fluorescein isothiocyanate (FITC), phycoerythrin (PE), peridinin chlorophyll protein (PerCP), allophycocyanin (APC), Texas Red, Alexa Fluor 488 (Molecular Probes, Inc., Eugene Oreg.), and the tandem fluorophores PerCP-Cy5.5, PE-Cy5, PE-Cy7, and APC-Cy7. Antibodies can also usefully be conjugated to biotin, permitting second stage detection using fluorophore-labeled streptavidin.

The methods of the present invention for detecting and enumerating antigen-specific T lymphocytes can be used for the same purposes as are prior art methods for detecting and enumerating antigen-specific T lymphocytes, including methods based upon surface labeling of TCR (use of MHC tetramers and MHC/Ig chimeras), as well as methods based upon detecting functional responses of antigen-specific T cells (limiting dilution assay, enzyme-linked immunospot assay, and flow cytometric detection of intracellular cytokine expression, Waldrop et al., *J. Clin. Invest.* 99(7):1739–50 (1997)). The methods can thus be used, e.g., to assess $CD4^+$ and $CD8^+$ T cell responses to infection, to vaccines, and in autoimmunity.

Depending upon the instrument used, detection of antigen-specific T lymphocytes can be coupled directly or indirectly to their sorting, thus providing, in other aspects of the invention, methods for enriching a sample in, and for depleting a sample of, T lymphocytes that are specific for a chosen antigen.

In general, these methods comprise contacting the sample with an intrinsically fluorescent multimeric complex of the present invention, wherein the peptide antigen of the complex is the chosen antigen and the MHC presenting domains of the complex are those for which the T lymphocytes desired to be enriched or depleted will be restricted, for a time and under conditions sufficient to permit detectable binding of the complex to T lymphocytes in the sample that are specific for the chosen antigen and MHC. After binding, labeled T lymphocytes are enriched or depleted based upon the fluorescence of the complex bound thereto.

Such methods are conveniently performed using a fluorescence activated cell sorter: sorting based at least in part upon fluorescence from the multimeric complex of the present invention directly depletes the sample from which the cells are removed and enriches the aliquot into which the cells are placed.

It is possible, however, to use the multimers of the present invention to enrich or deplete samples in T lymphocytes of particular antigen specificity using approaches other than fluorescence-activated cell sorting.

For example, T lymphocytes stained specifically with the multimer can be separated magnetically, rather than fluorimetrically, by further conjugation of the TCR-bound complex to a superparamagnetic particle. This can be done, e.g., using an antibody that is conjugated to a magnetic particle and that is specific for an epitope of the fusion protein (e.g., where DsRed contributes GFP-like chromophore and/or multimerization domains, the antibody can be the DsRed-specific antibody available commercially from Clontech Labs, Palo Alto, Calif., USA).

As another example, T lymphocytes stained specifically with the multimer can be separated using biotin/avidin affinity interactions, rather than fluorescence, by further conjugation of the TCR-bound complex to biotin, followed by use of an avidin affinity matrix. This further labeling of the multimeric complex can be done indirectly using a biotin-conjugated antibody specific for an epitope of the fusion protein. Alternatively, the multimer can itself be prior-conjugated to biotin, either chemically or, upon engineering of a BirA substrate peptide into the complex (typically the fusion protein), enzymatically.

Samples enriched in antigen-specific T cells according to the methods of the present invention can be used in vitro for study of specific interactions of antigen-specific T cells with antigen-presenting cells, cytotoxic targets, B cells, or other cellular elements of the immune system. Samples enriched in antigen-specific T cells according to the method of the present invention can also be used in vitro to modify such interactions. See, e.g., Dal Porto et al., et al., *Proc. Natl. Acad. Sci. USA* 90:6671–6675 (1993).

Samples enriched in antigen-specific T cells according to the methods of the present invention can also be used for in vivo therapeutic intervention, such as for tumor immunotherapy. See, e.g., Oelke et al., *Clin. Cancer Res.* 6(5): 1997–2005 (2000). Conversely, samples depleted in particular antigen-specific T cells according to the methods of the present invention can be advantageously administered to patients where infusion of blood fractions containing T cells having that antigen specificity would occasion disease or morbidity.

As an alternative utility to fluorescent detection of peptide specific T-cells, the multimeric protein complexes of the instant invention can also advantageously be used to stimulate peptide antigen-specific, MHC-dependent, activation of T cells.

As is known in the art, complexes comprising multiple MHC molecules loaded with peptide are more potent than non-complexed, monomeric MHC-peptide combinations for stimulating T-cells that specifically bind the peptide by a MHC dependent mechanism. See, for example, Stryhn A., et al., "Preformed purified peptide/major histocompatibility class I complexes are potent stimulators of class I-restricted T cell hybridomas," *Eur. J. Immunol.*, 24(6):1404–9 (June 1994); Cochran J. R., et al., "The relationship of MHC-peptide binding and T cell activation probed using chemically defined MHC class II oligomers," *Immunity,* 12(3): 241–50 (March 2000); and Piccirillo C. A., Shevach E. M., "Cutting edge: control of CD8+ T cell activation by CD4+ CD25+ immunoregulatory cells," *J. Immunol.,* 167(3):1137–40 (August 2001), the disclosure of each of which is incorporated herein by reference in its entirety.

Tetramers of MHC peptide-presenting moieties, formed by interaction of the multimerization domains contained within the DsRed subunits of the multimeric complexes of the instant invention, can therefore be loaded with peptide and incubated with a mixed population of T-cells. Subpopulations of T-cells bearing T-cell receptors capable of specifically binding the peptide in a MHC-dependent manner will be activated. The greater potency of the tetramers, as compared to monomers, dimers or trimers, facilitates activation of T-cells using lower concentration of peptide-MHC complexes. This lowers cost of reagents and decreases spurious activation caused by high concentrations of activating peptide-MHC complexes. Alternatively, the greater potency of tetramers facilitates activation of T-cell subpopulations bearing receptors with lower affinity for the peptide.

According to an alternative embodiment, clonal populations of T-cells with defined peptide specificity can all be activated using lower concentrations of tetrameric peptide-MHC complexes.

Thus, in another aspect, the present invention provides a method of activating peptide antigen-specific, MHC-dependent, T-cells, comprising contacting, for time sufficient to effect activation, a T-cell with an intrinsically fluorescent, self-multimerizing multimeric complex of the instant invention to which the peptide has been bound.

Kits

The multimeric complex compositions of the present invention can usefully be provided in the form of kits that facilitate the practice of the methods of the present invention. Thus, in another aspect, the present invention provides kits comprising the intrinsically fluorescent multimeric complexes of the present invention.

In one embodiment, the kits of the present invention include, as separate compositions, an intrinsically fluorescent $(F_1S_1)_n$ multimer of the present invention, and an antigenic peptide. As noted above, the choice of peptide will depend upon the specificity desired for the labeling reagent.

In some embodiments, a further composition, comprising a second, negative control, peptide is usefully included. The negative control peptide, when used to charge the intrinsically fluorescent $(F_1S_1)_n$ multimer of the kit, will provide a multimeric complex that has been prior shown not to label a significant percentage of T lymphocytes in the sample to be tested, thus providing a measure of the background attributable to nonspecific binding of the multimer to cells in the sample.

In other embodiments, the kit will further include at least one pan-T or T lymphocyte subsetting antibody. As noted above, by "pan-T antibody" is intended an antibody that recognizes a surface marker or epitope present on all, or substantially all, T lymphocytes. By "T cell subsetting antibody" is intended an antibody that binds to a surface marker present on fewer than all T lymphocytes.

Where the intrinsically fluorescent multimer is prior-charged with peptide, such kits typically will include, as separate compositions, a multimer and at least one pan-T or subsetting antibody; where the intrinsically fluorescent multimer is provided without prior-charging with peptide (i.e., as an $(F_1S_1)_n$ structure), the kit will usefully include as separate compositions an intrinsically fluorescent multimer, a peptide, and at least one pan-T or subsetting antibody.

Pan-T and subsetting antibodies usefully included in such kits include those specific for CD3, CD4, CD8, CD45RO, CD45RA, and CD27. As would be understood, the antibodies would typically be specific for the surface marker as expressed by T lymphocytes of the taxonomic species whose T lymphocytes are recognized by the intrinsically-fluorescent multimeric complex (e.g., anti-murine CD3 antibody in a kit that includes a multimeric complex having murine MHC peptide-presenting moieties and soluble derivatives).

In other embodiments, the kit will include at least one antibody to a T cell activation antigen. T cell activation antigens usefully included in such kits include those specific for CD69, CD25, CD71 and, for labeling human T lymphocytes, HLA-DR. Such kits can advantageously also include a pan-T and/or T cell subsetting antibody as above-described.

In kits that include antibodies, the antibodies are usefully provided prior-conjugated directly to a fluorophore, typically a fluorophore that is flow cytometrically distinguishable from the emission of the intrinsically fluorescent multimeric T cell labeling complex and from the emission of other fluorophores used in the kit. Fluorophores can usefully be selected from the group consisting of fluorescein isothiocyanate (FITC), phycoerythrin (PE), peridinin chlorophyll protein (PerCP), allophycocyanin (APC), Texas Red, Alexa Fluor 488 (Molecular Probes, Inc., Eugene Oreg.), and the tandem fluorophores PerCP-Cy5.5, PE-Cy5, PE-Cy7, and APC-Cy7. Antibodies in kits of the present invention can also usefully be conjugated to biotin, permitting second stage detection using labeled streptavidin.

Also usefully included in kit embodiments that include antibodies are isotype control antibodies; as is well known, such isotype control antibodies are antibodies of identical isotype to the fluorophore-conjugated antibodies but directed to irrelevant specificities, such as KLH, suitable to provide measurements of background binding and fluorescence.

Other kit embodiments further include a red blood cell lysing agent, as is described, inter alia, in Chang et al., U.S. Pat. Nos. 4,902,613 and 4,654,312; lysing agents are well known in the art and are available commercially from a number of vendors (FACS Lysing Solution, Becton Dickinson Biosciences Immunocytometry Systems, San Jose, Calif., USA; Cal-Lyse™ Lysing Solution, Caltag Labs, Burlingame, Calif., USA; No-Wash Lysing Solution, Beckman Coulter, Inc., Fullerton, Calif.).

Many of the kit embodiments will further include instructions for labeling (staining) with the multimeric complex and for performing flow cytometric analysis.

Other kit embodiments further include an antibody capable of specifically recognizing and binding DsRed, or other GFP-like chromophores, which antibody is conjugated to a fluorophore. In this manner, indirect immunofluorescence techniques can be employed. For example, in a first step, the intrinsically fluorescent, multimeric protein complex of the instant invention bearing peptide is incubated with T-cells to effect specific binding of peptide to T-cell receptors. Thereafter, in a second step, the fluorescently labeled secondary antibody is incubated with the T-cells such that the antibody binds the GFP-like chromophore bound to T-cells. For analysis, the fluorophore associated with the secondary antibody is stimulated with light of the appropriate wavelength, which typically, but not invariably, is chosen so as to avoid substantial stimulation of fluorescent emission by the GFP-like fluorophore.

Indirect immunofluorescence can also be accomplished in three steps. As for the two step method, a second antibody is used to bind the GFP-like chromophore; the second antibody, however, is not itself conjugated to a fluorophore. Rather, in a third step, a fluorescently labeled third antibody is added which is specific for, and binds to, the second antibody. During analysis, the fluorophore conjugated to the third antibody is stimulated by light of the appropriate wavelength. Thus, kits of the instant invention may further include a second antibody that recognizes the GFP-like chromophore and a fluorescently labeled third antibody that recognizes the second antibody.

As used herein, the term "antibody" encompasses whole antibodies, including, but not limited to, those of the IgG, IgM, IgA, IgE, and IgD classes; and antigen-specific antibody fragments, including, but not limited to, Fab, $(Fab')_2$, phage-displayed antibodies (phAb), and single-chain variable region antibodies (scFv).

The following examples are provided by way of illustration and not by way of limitation.

EXAMPLE 1

Construction of an Expression Vector for the Expression of a MHC-DsRed Fusion Protein Using standard molecular biology techniques, a DNA sequence encoding the extracellular domain (ECD) of murine H2-Ld MHC class I protein is removed from the H2-Ld CDNA and ligated into the Multiple Cloning Site of the vector pDsRed2-N1 (BD Biosciences-Clontech Cat. #6973-1) digested with the enzymes HindIII and BamHI. This results in an in-frame fusion of the coding sequence of the ECD, oriented at the amino-terminal part of the fusion, with the coding sequence of the DsRed chromophore, oriented at the carboxy-terminal part of the fusion. Construction of the fusion construct is shown schematically in FIG. 1.

Figure 2:
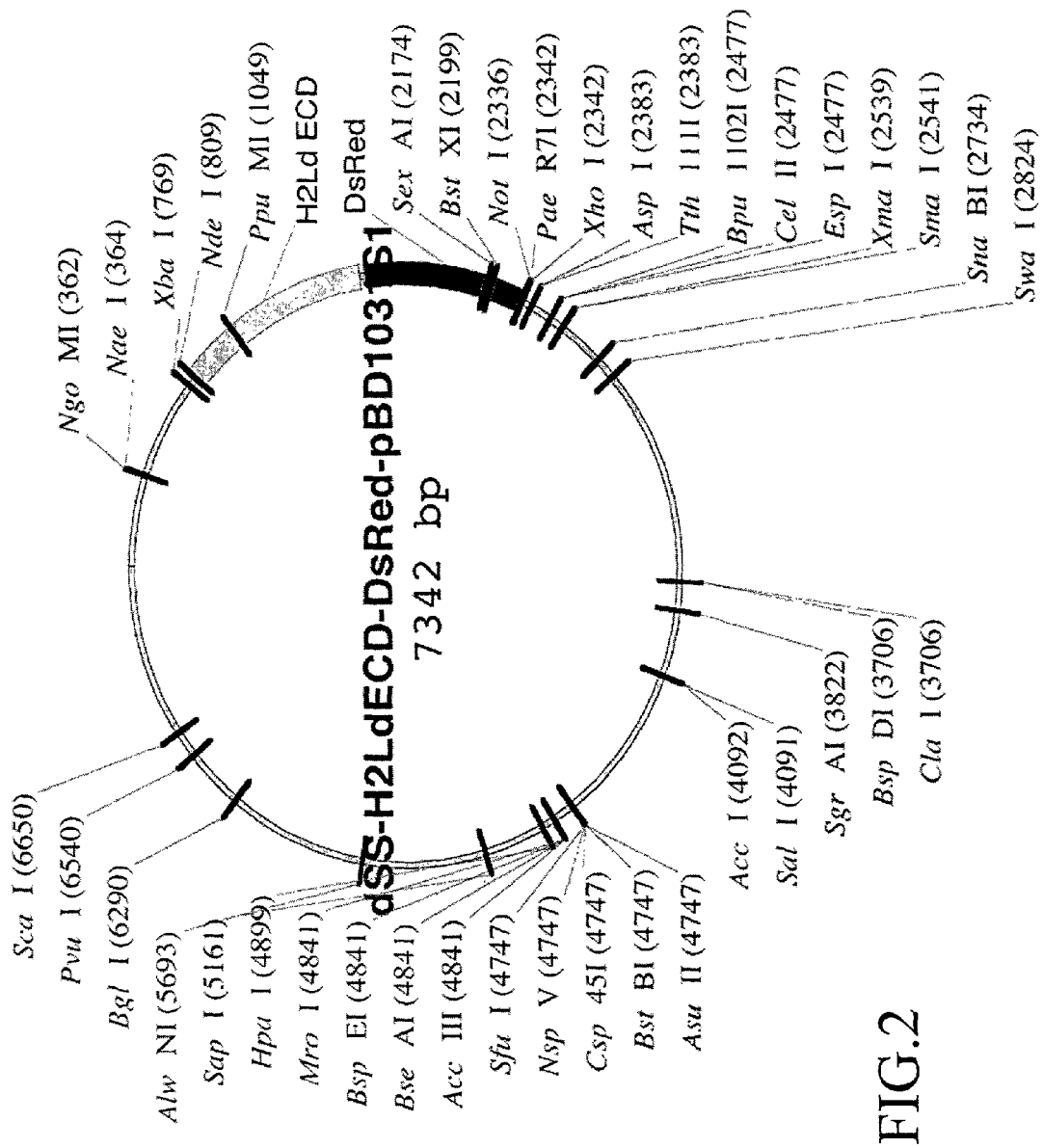
FIG. 2 schematizes a dual promoter expression vector containing the H2Ld-DsRed recombinant fusion construct according to the present invention.

The H2Ld-DsRed2 fusion construct is then ligated into the NdeI and NotI restriction enzyme sites of pBD1031S1, a BD Biosciences-Pharmingen vector developed from PVL1393, Cat. #21201P. The pBD1031S1 vector is a dual expression vector containing a T7 RNA polymerase promoter for expression of the fusion construct in bacteria and a baculovirus polyhedrin promoter for expression of the fusion construct in a variety of insect cell lines, including Sf9 and Tni cells. A schematic and restriction enzyme map of the expression vector, called dSS-H2LdECD-DsRed-pBD1031S1, is shown in FIG. 2.

After completion of the ligation reaction, using standard techniques, the ligated DNA is purified and used to transform *E. coli*. bacteria that are then grown overnight on agar plates containing ampicillin to select for transformed cells. Individual amp resistant colonies are then grown in liquid culture; aliquots of bacteria are withdrawn, from which plasmid DNA is isolated and purified.

Figure 3:
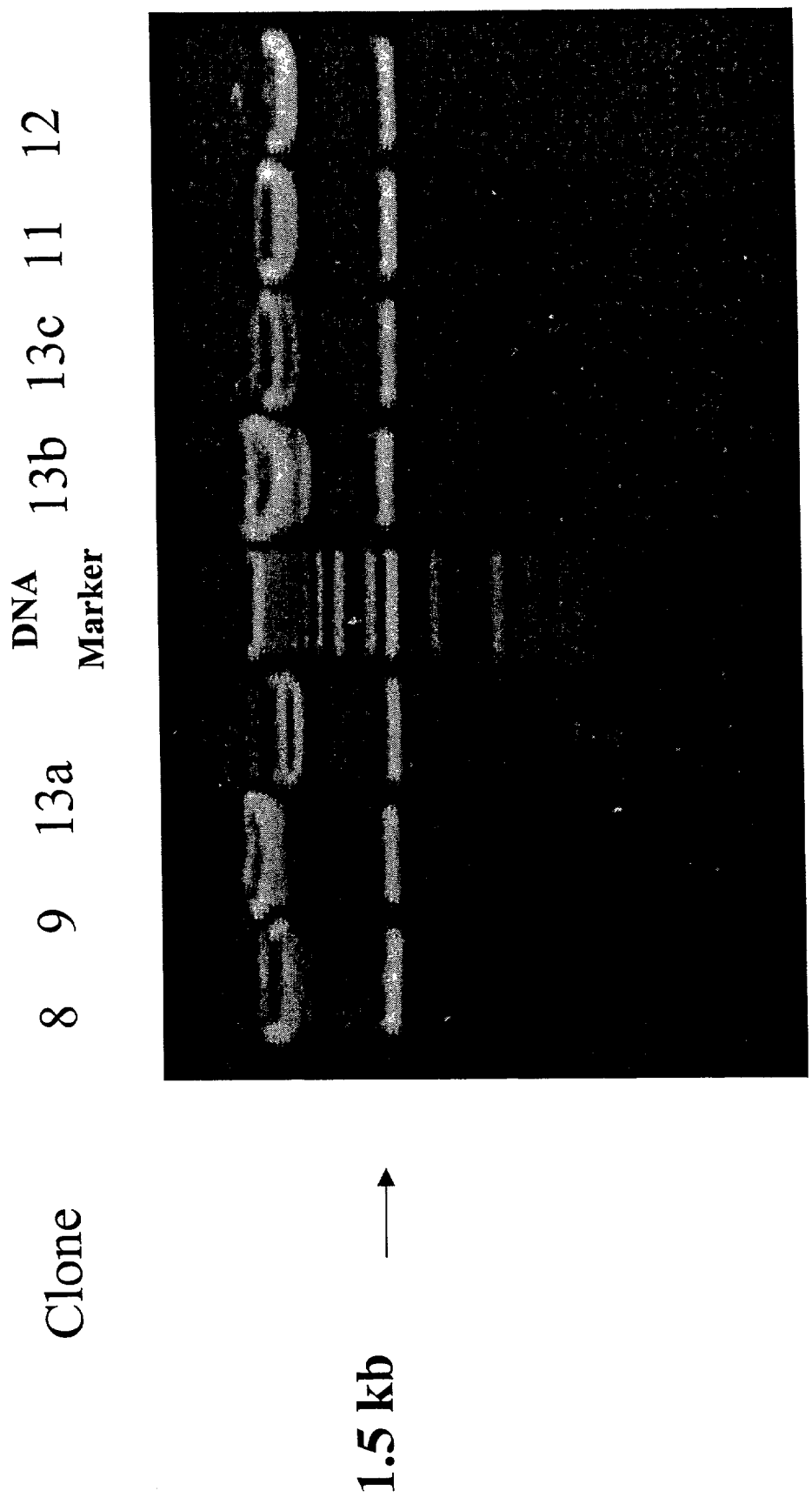
FIG. 3 is a photograph of an agarose gel showing the expected 1.5 kD H2Ld-DsRed recombinant fusion construct insert upon release from expression vector plasmids digested with NdeI and NotI.

Plasmid DNA is then doubly digested with NdeI and NotI restriction enzymes to test for the presence in the vector of the Ld-DsRed insert. The digests are separated by electrophoresis in 0.7% agarose gel that is then stained with ethidium bromide, or other fluorescent DNA dye, illuminated with UV light and photographed using a video still camera. Plasmids containing the expected 1.5 kb insert are reserved for further analysis by sequencing (see below) to confirm presence of the fusion construct insert. A photograph of an agarose gel showing the presence in seven plasmid clones of a 1.5 kb insert released by NdeI/NotI digestion is shown in FIG. 3.

Figure 4:
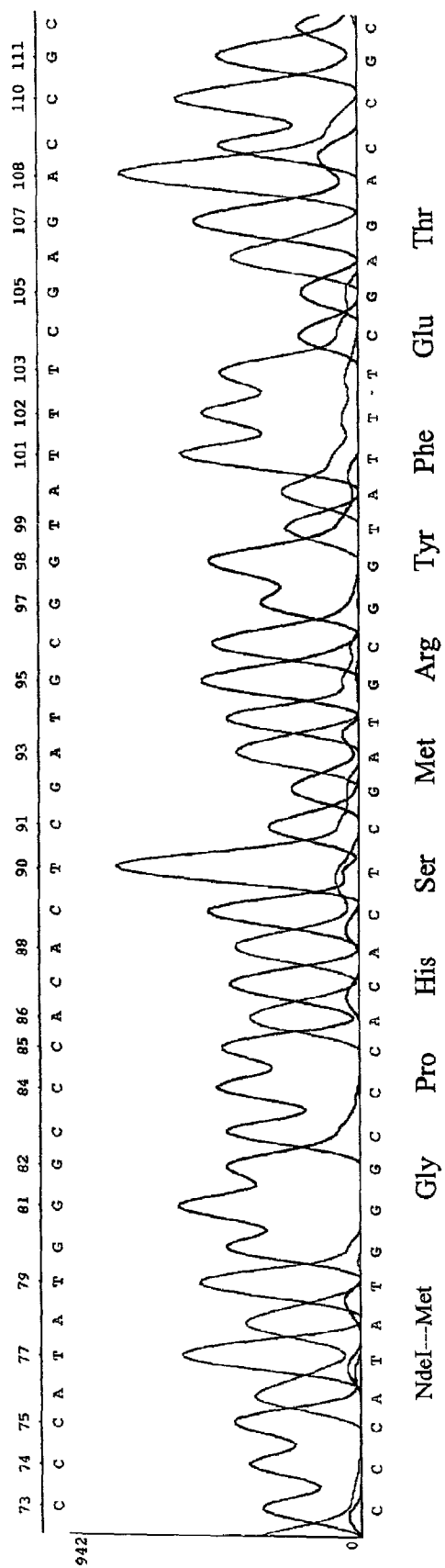
FIG. 4 is an automatic DNA sequencer trace further confirming the correct DNA sequence at the junction between the expression vector backbone and the H2Ld insert.

Following identification of insert-positive plasmid clones, the clones are sequenced, using standard techniques, across the NdeI juncture between the expression vector and the DNA sequence of the H2Ld ECD to confirm the absence of the signal peptide sequence and the presence of the correct amino terminal coding sequence. An automated sequencer sequence trace from sequencing of a clone with the correct amino terminal coding sequence is shown in FIG. 4.

EXAMPLE 2

Expression of the H2Ld-DsRed Fusion Protein in Bacteria

Using standard techniques, five clones of the H2Ld-DsRed fusion construct expression vector are used to transform competent *E. coli* bacteria containing an IPTG inducible T7 RNA polymerase. After growth overnight on ampicillin-LB agar plates, colonies of transformed cells are picked and expanded by growth overnight in LB media. The next day, the overnight culture is further grown at 37° C. in fresh LB media containing IPTG (final concentration 1 mM) for 2 hours.

Samples of bacteria from induced cultures are then withdrawn and lysed in an SDS-containing buffer, after which the constituent proteins are separated by SDS denaturing polyacrylamide gel electrophoresis (PAGE). After electrophoresis, gels are stained with Coomassie stain, after which the separated, stained proteins are illuminated by visible light and photographed with a video still camera for visual analysis.

Figure 5:
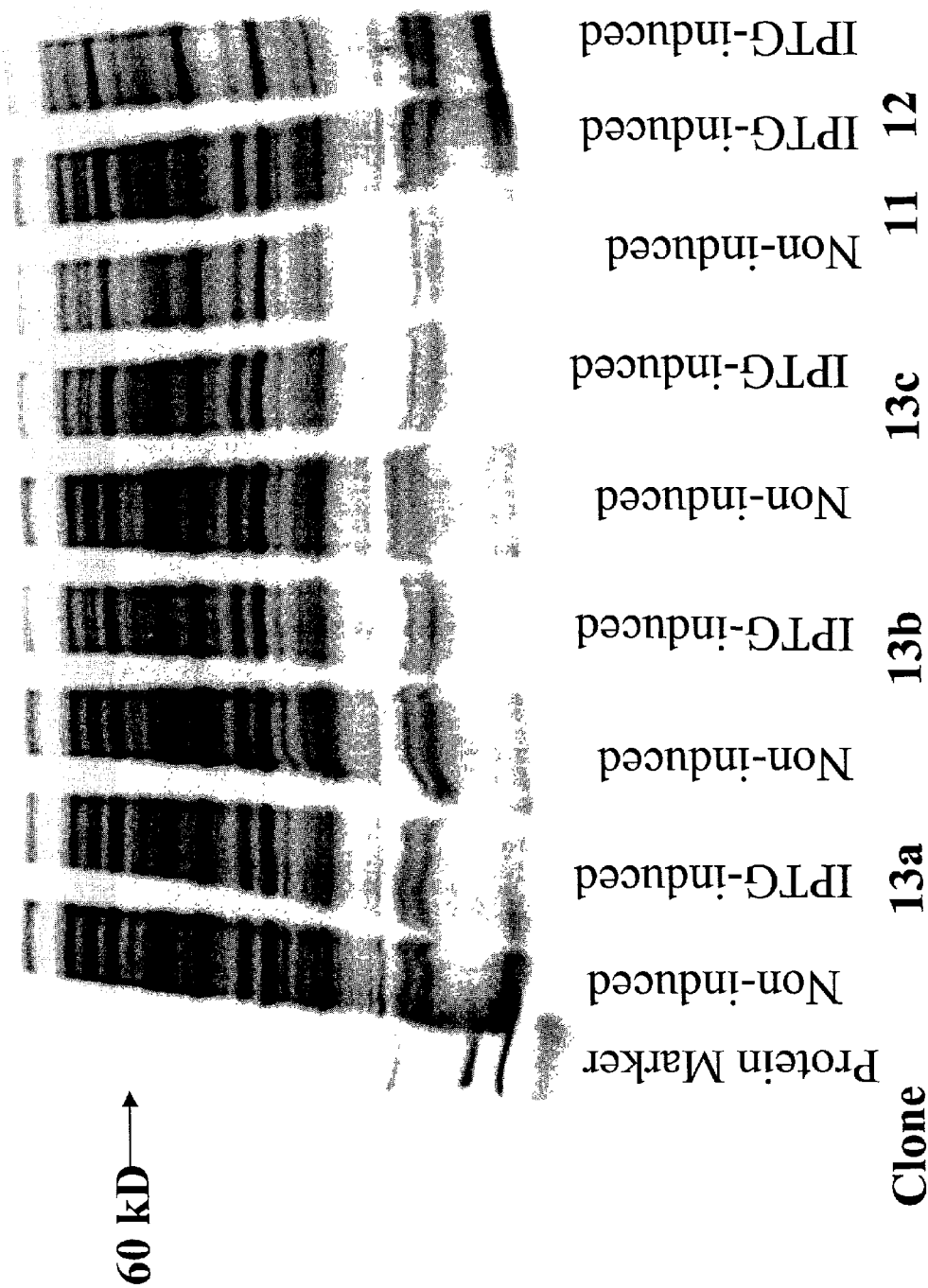
FIG. 5 is a photograph of a stained SDS-PAGE gel showing induction by IPTG of H2Ld-DsRed recombinant fusion protein in transformed E. coli.

As shown in FIG. 5, for each of five H2Ld-DsRed fusion construct expression vectors used to transform *E. coli*, induction with IPTG results in expression of a 60 kD protein, which matches the expected molecular mass of the H2Ld-DsRed fusion protein. In contrast, the induced 60 kD band is absent from negative controls that were not IPTG-induced (FIG. 5).

Figure 6:
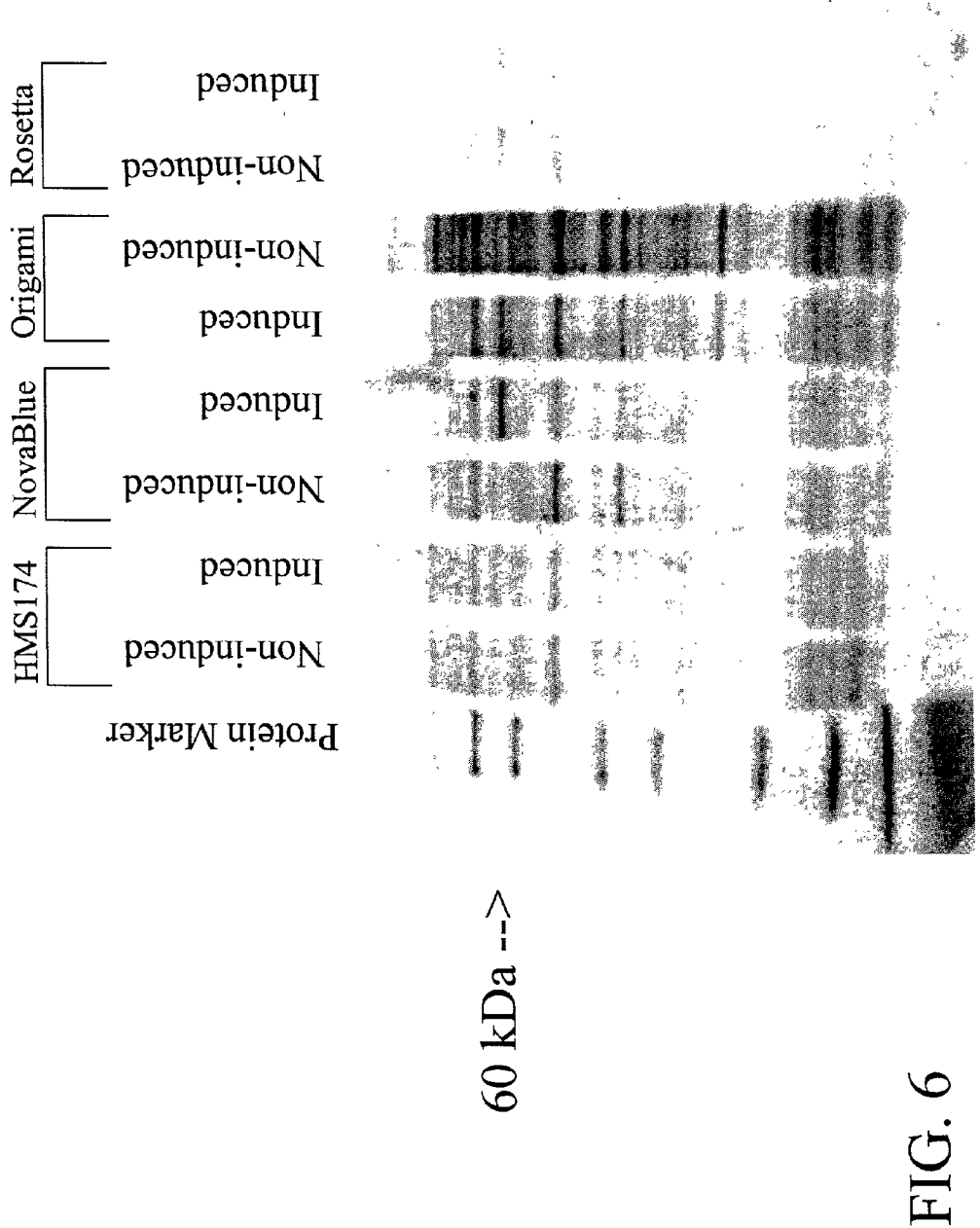
FIG. 6 is a photograph of a stained SDS-PAGE gel showing induction by IPTG of H2Ld-DsRed recombinant fusion protein in different transformed E. coli strains.

As shown in FIG. 6, the degree of IPTG-dependent induction is dependent on the strain of *E. coli* transformed with a H2Ld-DsRed expression vector: the "NovaBlue" and "Origami" strains show strong IPTG induction of a 60 kD protein. Using standard techniques, Western blot analysis of the gel stained with an anti-DsRed antibody confirms that the 6OkD band contains DsRed protein (data not shown).

EXAMPLE 3

Expression of the H2Ld-DsRed Fusion Protein in Insect Cells

The H2Ld-DsRed expression vector is cotransfected with BaculoGold™ DNA (BD-Pharmingen, Cat. No. 554739, formerly Cat. No. 21100D) into Sf9 and Tni insect cells using standard techniques discussed in the BD BaculoGold™ Linearized Baculovirus DNA technical data sheet, incorporated herein by reference in its entirety, and available from Pharmingen (BD Bioscience Pharmingen, San Diego, Calif. The expression vector serves as a transfer vector that complements a deletion in the BaculoGold™ virus DNA such that infectious virus is produced that contains within its genome the DNA encoding the H2Ld-DsRed fusion protein. Three days after transfection performed using standard techniques, medium from the transfected cell cultures is collected, cells are removed, and the supernatant is used in the first of three rounds of amplification to obtain a high titer stock solution of infectious baculovirus.

Figure 7:
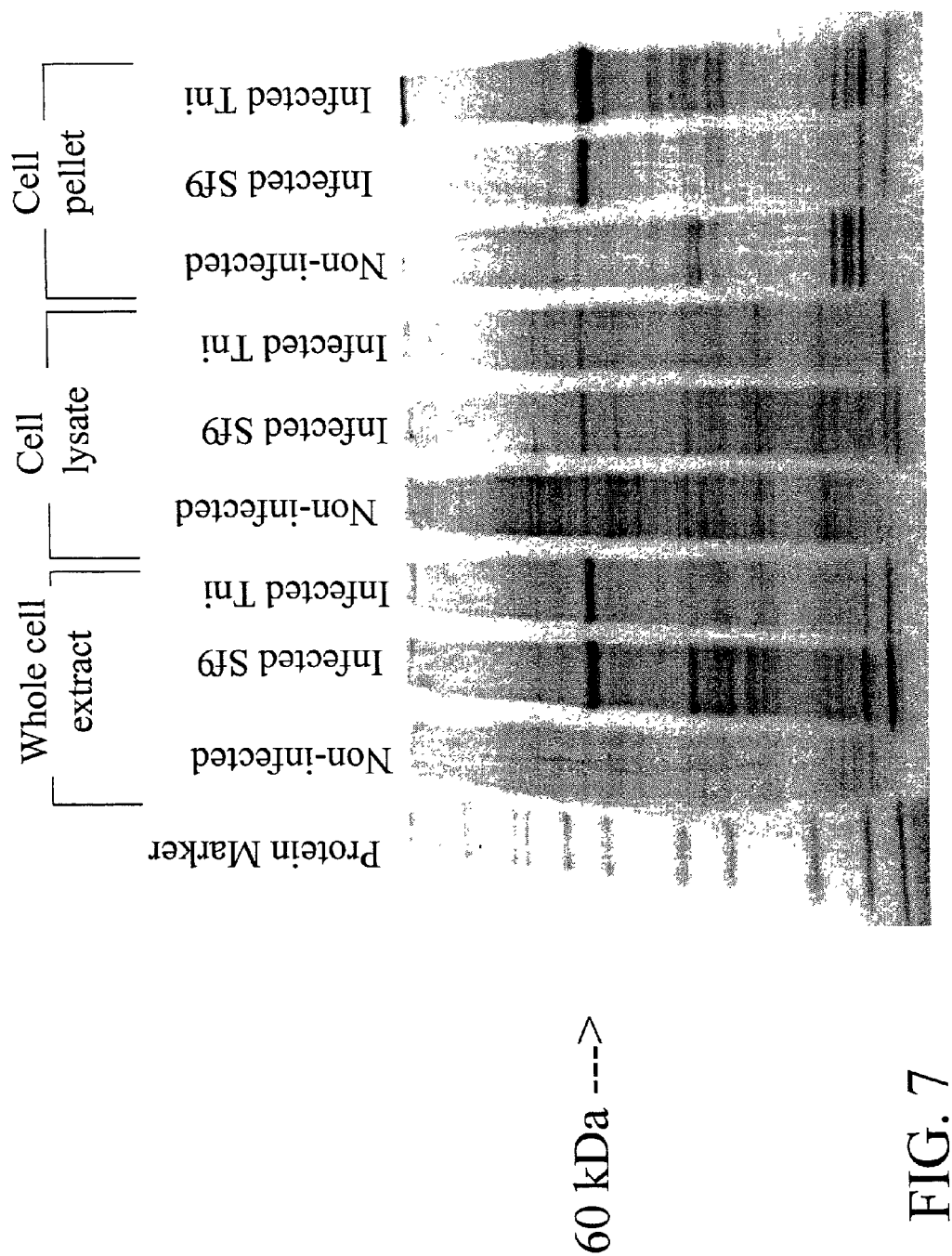
FIG. 7 is a photograph of a stained SDS-PAGE gel showing expression of H2Ld-DsRed recombinant fusion protein in insect cells infected with H2Ld-DsRed recombinant baculovirus.

Using standard techniques, the high titer stock is then used to infect Sf9 and Tni cells for the production of recombinant H2Ld-DsRed protein. Infected cells are solubilized with SDS-buffer and analyzed by SDS-PAGE, as described above for transformed and IPTG-induced bacteria. As shown in FIG. 7, a 60 kD protein band is expressed by infected Sf9 and Tni cells, but not by negative control, non-infected cells. Using standard techniques, Western blot analysis of the gel stained with an anti-DsRed antibody confirms that the 60 kD band contains DsRed protein (data not shown).

EXAMPLE 4

Fluorescence Detection of DsRed in H2Ld-DsRed Infected Insect Cells

Using standard techniques of fluorescence microscopy, insect cells infected with the H2Ld-DsRed fusion construct recombinant baculovirus produced as described in Example 3 are analyzed for expression of the H2Ld-DsRed fusion protein. Infected cells that produce H2Ld-DsRed fusion protein containing a functional DsRed chromophore are expected to emit red light by fluorescent emission.

Figure 8:
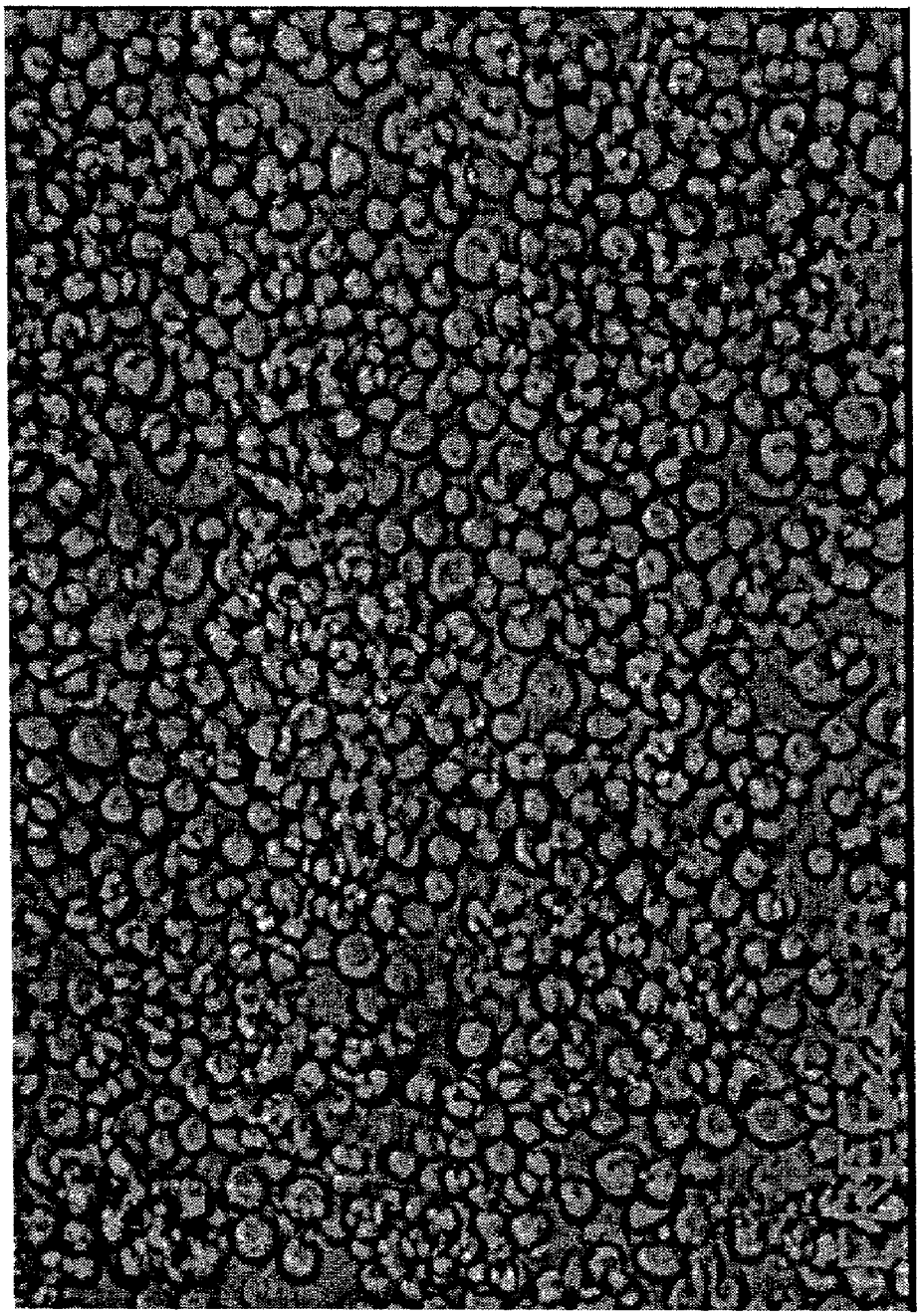
FIG. 8 is a photograph by conventional microscopy of non-infected Sf9 cells grown three days in culture.
Figure 9:
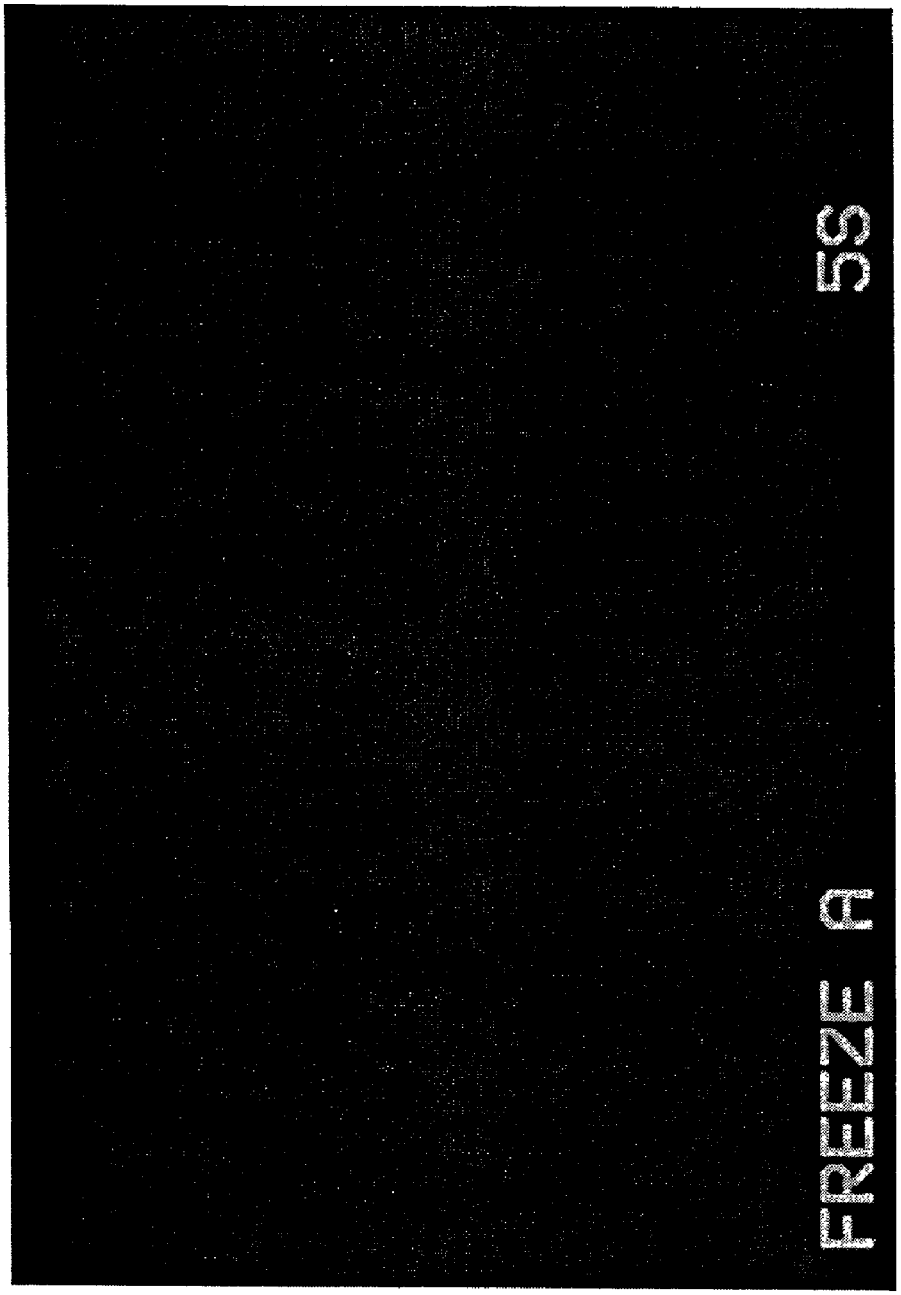
FIG. 9 is a photograph by fluorescent microscopy using a rhodamine filter of non-infected Sf9 cells grown three days in culture.

FIG. 8 shows negative control, non-infected Sf9 cells after three days of growth in culture by conventional light microscopy. As shown in FIG. 9, negative control Sf9 cells produce no red fluorescent emission when stimulated and analyzed by fluorescent microscopy three days post-infection.

Figure 10:
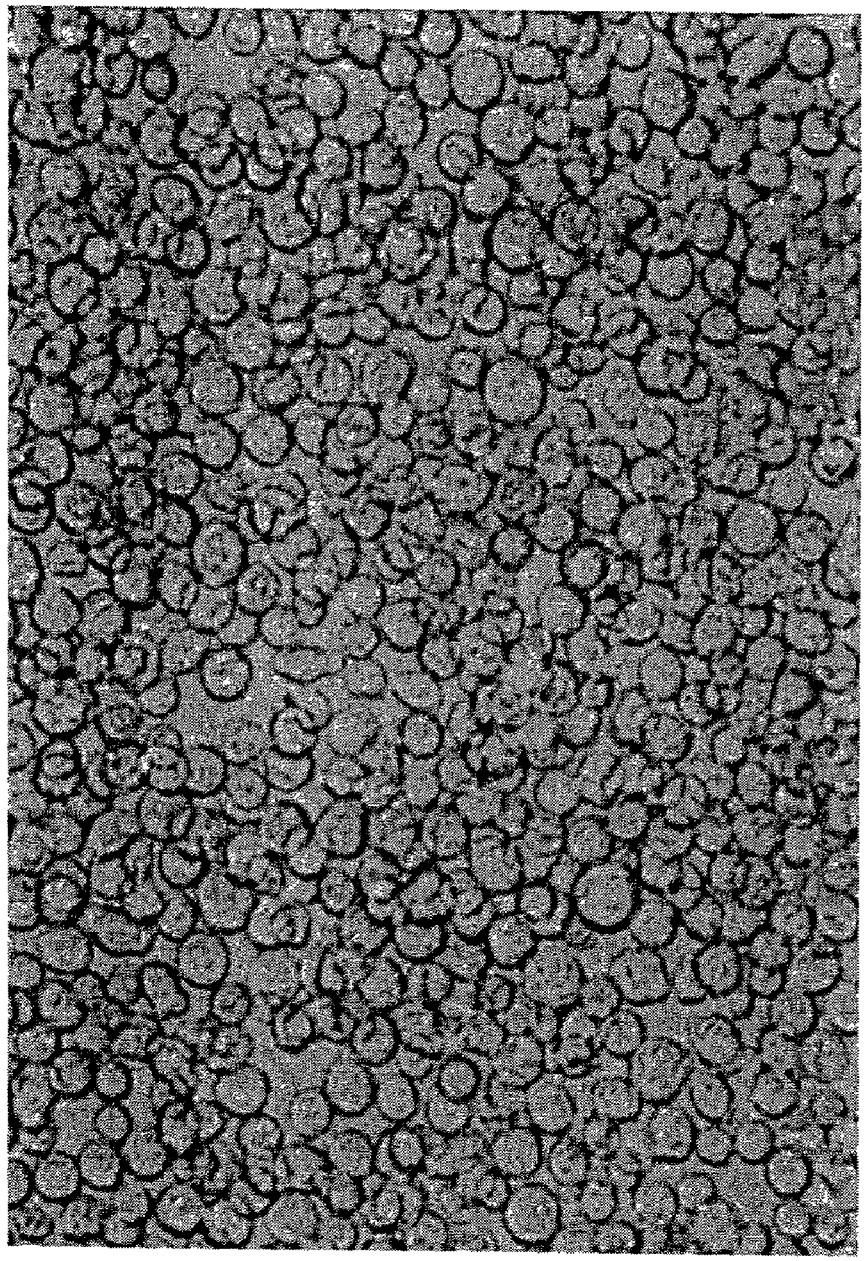
FIG. 10 is a photograph by conventional microscopy of Sf9 cells infected with the H2Ld-DsRed recombinant baculovirus grown three days in culture post-infection.

In contrast, FIG. 10 shows Sf9 cells infected with H2Ld-DsRed fusion construct recombinant baculovirus by conventional light microscopy after three days of growth in culture post-infection. As shown in FIG. 11, infected Sf9 cells emit red fluorescent light when stimulated and analyzed by fluorescent microscopy three days post-infection. Fluorescent emission of red light indicates that functional (and thus almost certainly tetramerized) DsRed chromophore is produced by the Sf9 cells infected with the H2Ld-DsRed fusion.

Figure 12:
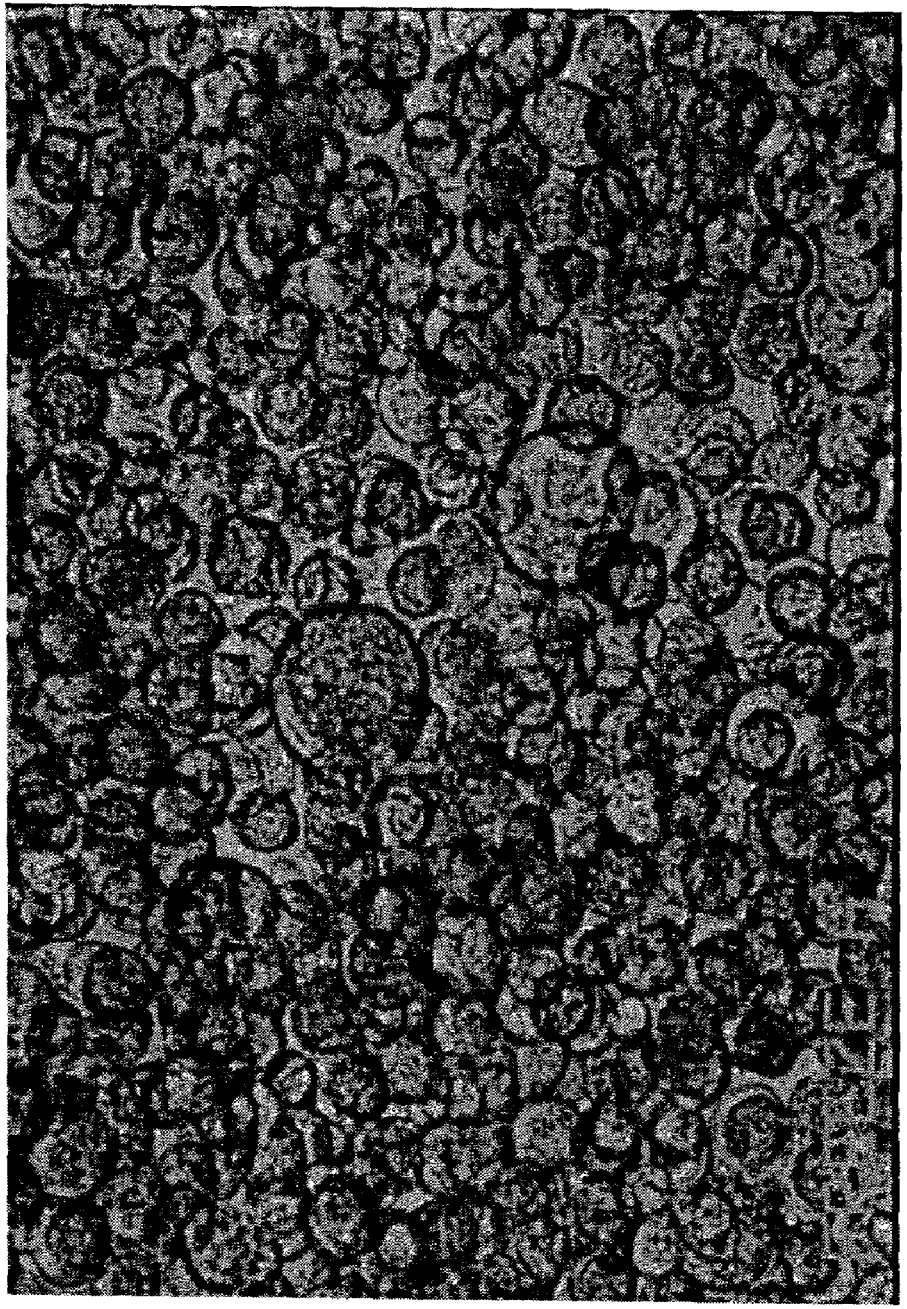
FIG. 12 is a photograph by conventional microscopy of Tni cells infected with the H2Ld-DsRed recombinant baculovirus grown three days in culture post-infection.

Similar results are seen with Tni insect cells. FIG. 12 shows Tni cells infected with H2Ld-DsRed fusion construct recombinant baculovirus by conventional light microscopy after three days of growth in culture post-infection. As shown in FIG. 13, infected Tni cells emit red fluorescent light when stimulated and analyzed by fluorescent microscopy three days post-infection. Fluorescent emission of red light indicates that functional DsRed chromophore is produced by the infected Tni cells.

All patents and publications cited in this specification are herein incorporated by reference as if each had specifically and individually been incorporated by reference herein. Although the foregoing invention has been described in some detail by way of illustration and example, it will be readily apparent to those of ordinary skill in the art in light of the teachings herein that certain changes and modifications may be made thereto without departing from the spirit or scope of the appended claims, which, along with their full range of equivalents, alone define the scope of invention.

What is claimed is:

1. A recombinant fusion protein, comprising:
   a GFP-like chromophore;
   at least one self-multimerization domain of a protein; and
   an MHC peptide-presenting moiety.

2. A nucleic acid, comprising: a sequence that encodes the fusion protein of claim 1 or is complementary to the sequence that encodes the fusion protein of claim 1.

3. A recombinant vector, comprising: the nucleic acid of claim 2.

4. The recombinant vector of claim 3, wherein said vector is capable of directing expression of said fusion protein in a host cell.

5. An isolated host cell, said host cell comprising:
   the recombinant vector of claim 4.

6. An intrinsically fluorescent, multimeric protein complex, comprising:
   a plurality of subunits, said subunits having the quaternary formula in said complex of $(F)_n$, wherein F is a fusion protein according to claim 1 and n is an integer greater than 1.

7. An intrinsically fluorescent, multimeric protein complex, comprising:
   a plurality of subunits, said subunits having the quaternary formula in said complex of $(FS)_n$, wherein
   F is a recombinant fusion protein according to claim 1;
   S is a soluble protein selected from the group consisting of (β2 microglobulin, class II β MHC peptide-presenting soluble derivatives, and class II α MHC peptide-presenting soluble derivatives;
   S β2 microglobulin when F includes a class I α MHC peptide-presenting moiety, S is a class II β MHC peptide-presenting soluble derivative when F includes a class II α MHC peptide-presenting moiety, and S is a class II α MHC peptide presenting soluble derivative when F includes a class II β MHC peptide-presenting moiety; and
   n is an integer greater than 1.

8. An intrinsically fluorescent, multimeric protein complex for labeling T lymphocytes according to the specificity of their antigen receptors, comprising:
   a plurality of subunits, said subunits having the quaternary formula in said complex of $(FSP)_n$, wherein
   F is a recombinant fusion protein according to claim 1;
   S is a soluble protein selected from the group consisting of β2 microglobulin, class II β MHC peptide-presenting soluble derivatives, and class II α MHC peptide-presenting soluble derivatives;
   S is β2 microglobulin when F includes a class I α MHC peptide-presenting moiety, S is a class II β MHC peptide-presenting soluble derivative when F includes a class II α MHC peptide-presenting moiety, and S is a class II α MHC peptide presenting soluble derivative when F includes a class II β MHC peptide-presenting moiety;
   P is a peptide antigen; and
   is an integer greater than 1.

9. A recombinant fusion protein, comprising:
   a means for fluorescing, said means encoded entirely within the amino acid sequence of said protein;
   a means for self-multimerizing; and
   a means that is capable of contributing to presentation of a peptide antigen to an MHC-restricted T lymphocyte.

10. An intrinsically fluorescent, multimeric protein complex for labeling T lymphocytes according to the specificity of their antigen receptors, comprising:
- a means for fluorescing, encoded entirely within an amino acid sequence of at least one subunit of said multimeric complex;
- a means for self-multimerizing encoded entirely within an amino acid sequence of at least one subunit of said multimeric complex; and
- a means for binding to a T lymphocyte according to the specificity of its antigen receptor.

11. A method for detectably labeling a T lymphocyte according to the specificity of its antigen receptor, the method comprising:
- contacting said T lymphocyte with an intrinsically fluorescent multimeric complex according to claim 8, the antigen receptor of said T lymphocyte being specific for the peptide antigen and the MHC presenting domains of said complex, for a time and under conditions sufficient to permit detectable binding of said complex to said T lymphocyte.

12. A method for detecting, in a sample of cells, T lymphocytes that are specific for a chosen antigen, comprising:
- contacting said sample with an intrinsically fluorescent multimeric complex according to claim 8, wherein the peptide antigen of the complex is the chosen antigen and the MHC presenting domains of the complex are those for which the T lymphocytes desired to be detected will be restricted, for a time and under conditions sufficient to permit detectable binding of said complex to T lymphocytes specific for said chosen antigen; and then
- detecting specific T lymphocytes in said sample by the fluorescence of the complex bound thereto.

13. The method of 12, further comprising: enumerating the antigen-specific T lymphocytes so detected.

14. The method of claim 12, further comprising:
- contacting said sample with at least one fluorophore-conjugated antibody, said antibody selected from the group consisting of pan-T antibodies and T cell subsetting antibodies;
- detecting cell-bound fluorescence of the multimeric fluorescent complex; and
- detecting cell-bound fluorescence from the at least one fluorophore-conjugated antibody.

15. The method of claim 12, further comprising:
- contacting said sample with at least one fluorophore-conjugated antibody specific for a T cell activation antigen, and then
- detecting activated specific T lymphocytes in said sample by the fluorescence of the multimeric fluorescent complex and at least one fluorophore-conjugated antibody bound thereto.

16. A method for enriching a sample in T lymphocytes that are specific for a chosen antigen, comprising;
- contacting said sample with an intrinsically fluorescent multimeric complex according to claim 8, wherein the peptide antigen of said complex is said chosen antigen, for a time and under conditions sufficient to permit detectable binding of said complex to T lymphocytes specific for said chosen antigen; and then
- enriching for said specific T lymphocytes based upon the fluorescence of the complex bound thereto.

17. A method for depleting a sample of T lymphocytes that are specific for a chosen antigen, comprising:
- contacting said sample with an intrinsically fluorescent multimeric complex according to claim 8, wherein the peptide antigen of said complex is said chosen antigen, for a time and under conditions sufficient to permit detectable binding of said complex to T lymphocytes specific for said chosen antigen; and then
- depleting said sample of specific T lymphocytes based upon the fluorescence of the complex bound thereto.

18. A kit comprising, as separate compositions:
the multimeric complex of claim 7; and
a peptide antigen.

19. The kit of claim 18, further comprising:
- a fluorophore-conjugated antibody selected from the group consisting of pan-T antibody and T cell subsetting antibody.

20. The kit of claim 18 or claim 19, further comprising:
- a fluorophore-conjugated antibody specific for a T cell activation antigen.

21. A kit comprising, as separate compositions:
the multimeric complex of claim 8; and
- a fluorophore-conjugated antibody selected from the group consisting of pan-T antibody and T cell subsetting antibody.

22. The kit of claim 21, further comprising:
- a fluorophore-conjugated antibody specific for a T cell activation antigen.

23. The kit of either of claims 18 or 21, further comprising:
a red blood cell lysing agent.

24. The recombinant fusion protein of claim 1, further comprising a flexible peptide spacer.

* * * * *